(12) United States Patent
Sun et al.

(10) Patent No.: US 12,213,818 B2
(45) Date of Patent: Feb. 4, 2025

(54) X-RAY IMAGING SYSTEM FOR RADIATION THERAPY

(71) Applicant: SHANGHAI UNITED IMAGING HEALTHCARE CO., LTD., Shanghai (CN)

(72) Inventors: Buliang Sun, Shanghai (CN); Cheng Ni, Shanghai (CN); Wei Zhang, Shanghai (CN); Li Wang, Shanghai (CN); Hongjun Zhang, Shanghai (CN); Jian Zhang, Shanghai (CN); Tao Liu, Shanghai (CN); Can Liao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 18/180,837

(22) Filed: Mar. 8, 2023

(65) Prior Publication Data
US 2023/0218248 A1 Jul. 13, 2023

Related U.S. Application Data

(63) Continuation of application No. PCT/CN2021/110163, filed on Aug. 2, 2021, which
(Continued)

(30) Foreign Application Priority Data

Nov. 7, 2020 (CN) .......................... 202011234813.9
Nov. 13, 2020 (CN) .......................... 202011271345.2
(Continued)

(51) Int. Cl.
*A61N 5/10* (2006.01)
*A61B 6/40* (2024.01)
*A61B 6/42* (2024.01)

(52) U.S. Cl.
CPC .............. *A61B 6/4007* (2013.01); *A61B 6/42* (2013.01); *A61N 5/1045* (2013.01); *A61N 5/1081* (2013.01)

(58) Field of Classification Search
None
See application file for complete search history.

(56) References Cited

U.S. PATENT DOCUMENTS

| 6,661,870 B2 | 12/2003 | Kapatoes et al. |
| 2003/0048868 A1* | 3/2003 | Bailey .................... A61B 6/032 378/65 |

(Continued)

FOREIGN PATENT DOCUMENTS

| CN | 107184225 A | 9/2017 |
| CN | 207765764 U | 8/2018 |

(Continued)

OTHER PUBLICATIONS

International Search Report in PCT/CN2021/138130 mailed on Mar. 11, 2022, 5 pages.
(Continued)

*Primary Examiner* — Hoon K Song
(74) *Attorney, Agent, or Firm* — METIS IP LLC

(57) ABSTRACT

The present disclosure may provide a radiation system including a first rotation portion, a second rotation portion, a treatment head, one or more imaging sources, and at least one detector. At least a portion of the treatment head may be disposed in the first rotation portion. At least one of the one or more imaging sources may be disposed in the second
(Continued)

rotation portion. The second rotation portion may be able to rotate independently from the first rotation portion.

20 Claims, 15 Drawing Sheets

Related U.S. Application Data is a continuation-in-part of application No. 17/015,033, filed on Sep. 8, 2020, now Pat. No. 11,883,687.

(30) Foreign Application Priority Data

| Dec. 14, 2020 | (CN) | ......................... 202011468108.5 |
| Mar. 12, 2021 | (WO) | ................ PCT/CN2021/080638 |
| Mar. 12, 2021 | (WO) | ................ PCT/CN2021/080639 |

(56) References Cited

U.S. PATENT DOCUMENTS

| 2006/0074304 | A1 | 4/2006 | Sayeh |
| 2007/0003007 | A1 | 1/2007 | Carrano et al. |
| 2007/0003021 | A1 | 1/2007 | Guertin et al. |
| 2007/0003123 | A1 | 1/2007 | Fu et al. |
| 2007/0016014 | A1 | 1/2007 | Hara et al. |
| 2007/0211856 | A1 | 9/2007 | Urano et al. |
| 2008/0002809 | A1 | 1/2008 | Bodduluri |
| 2008/0205588 | A1 | 8/2008 | Kim |
| 2010/0290586 | A1 | 11/2010 | Friedrich |
| 2011/0040170 | A1 | 2/2011 | Geva et al. |
| 2011/0182410 | A1 | 7/2011 | Balakin |
| 2012/0035470 | A1* | 2/2012 | Kuduvalli .............. A61B 6/032 600/427 |
| 2012/0129360 | A1 | 5/2012 | Angerpointner et al. |
| 2012/0230465 | A1 | 9/2012 | Matsuzawa et al. |
| 2013/0256551 | A1 | 10/2013 | Yao |
| 2013/0266202 | A1 | 10/2013 | Yamada et al. |
| 2014/0247919 | A1 | 9/2014 | Zhang et al. |
| 2015/0182175 | A1 | 7/2015 | Handa et al. |
| 2016/0262709 | A1 | 9/2016 | Siewerdsen et al. |
| 2016/0303401 | A1* | 10/2016 | Mostafavi .............. A61B 6/107 |
| 2017/0106208 | A1 | 4/2017 | Gauthier et al. |
| 2018/0192978 | A1 | 7/2018 | Naylor et al. |
| 2018/0304098 | A1 | 10/2018 | Humber et al. |
| 2019/0000406 | A1 | 1/2019 | Liu et al. |
| 2019/0168025 | A1 | 6/2019 | Koponen et al. |
| 2019/0175945 | A1 | 6/2019 | Yan et al. |
| 2019/0209868 | A1 | 7/2019 | Stahl et al. |
| 2019/0209869 | A1 | 7/2019 | Liu et al. |
| 2019/0336793 | A1 | 11/2019 | Zhou et al. |
| 2019/0336795 | A1 | 11/2019 | Zhou et al. |
| 2019/0380666 | A1 | 12/2019 | Sheng et al. |
| 2020/0170591 | A1 | 6/2020 | Gagnon et al. |
| 2020/0406064 | A1 | 12/2020 | Maltz et al. |
| 2021/0030380 | A1 | 2/2021 | Subrahmanyam et al. |
| 2021/0267683 | A1* | 9/2021 | Brown .................. A61B 6/037 |

FOREIGN PATENT DOCUMENTS

| CN | 108514694 A | 9/2018 |
| CN | 109224320 A | 1/2019 |
| CN | 214013363 U | 8/2021 |
| CN | 215605797 U | 1/2022 |
| EP | 3056245 A1 | 8/2016 |
| WO | 2012055098 A1 | 5/2012 |
| WO | 2012099747 A2 | 7/2012 |
| WO | 2018093933 A1 | 5/2018 |
| WO | 2018176016 A1 | 9/2018 |

OTHER PUBLICATIONS

Written Opinion in PCT/CN2021/138130 mailed on Mar. 11, 2022, 5 pages.
International Search Report in PCT/CN2021/110163 mailed on Sep. 28, 2021, 5 pages.
Written Opinion in PCT/CN2021/110163 mailed on Sep. 28, 2021, 6 pages.
International Search Report in PCT/CN2021/080639 mailed on Aug. 19, 2021, 5 pages.
Written Opinion in PCT/CN2021/080639 mailed on Aug. 19, 2021, 5 pages.

* cited by examiner

X-RAY IMAGING SYSTEM FOR RADIATION THERAPY

CROSS-REFERENCE TO THE RELATED APPLICATIONS

This application is a continuation of International Patent Application No. PCT/CN2021/110163, filed on Aug. 2, 2021, which claims priority of U.S. patent application Ser. No. 17/015,033 filed on Sep. 8, 2020, Chinese Application No. 202011234813.9 filed on Nov. 7, 2020, Chinese Application No. 202011271345.2 filed on Nov. 13, 2020, Chinese Application No. 202011468108.5 filed on Dec. 14, 2020, International Application No. PCT/CN2021/080639 filed on Mar. 12, 2021, and International Application No. PCT/CN2021/080638, filed on Mar. 12, 2021, the contents of each of which are hereby incorporated by reference.

TECHNICAL FIELD

The present disclosure generally relates to medical technology, and more particularly, systems and methods for imaging systems for radiation therapy.

BACKGROUND

Radiation therapy is a localized treatment for a specific target tissue (a target volume), such as a cancerous tumor. Dosimetric and geometric data are checked before, after, or during the treatment, to ensure correct patient placement and that the administered radiotherapy treatment matches the previously planned treatment. This process is referred to as image-guided radiation therapy (IGRT), and involves the use of an imaging system to view target tissues while radiation treatment is delivered to the target volume.

SUMMARY

According to one aspect of the present disclosure, a radiation system may be provided. The radiation system may include a first rotation portion; a second rotation portion; a treatment head, at least a portion of the treatment head being disposed in the first rotation portion; one or more imaging sources, at least one of the one or more imaging sources being disposed in the second rotation portion; and at least one detector. The second rotation portion may be able to rotate independently from the first rotation portion.

In some embodiments, the one or more imaging sources may include at least one of: a first imaging source configured to emit a first imaging beam towards an object, the first imaging source being disposed in the second rotation portion; or at least one second imaging source configured to emit at least one second imaging beam towards an object.

In some embodiments, at least two of the first imaging source and the at least one second imaging source may share one of the at least one detector.

In some embodiments, the at least one detector may include at least one of: a first detector configured to detect at least a portion of the first imaging beam, the first detector being disposed in the second rotation portion; or at least one second detector configured to detect at least a portion of the at least one second imaging beam.

In some embodiments, the at least one second imaging source or the at least one second detector may be fixed at a fixed position of a room housing at least a portion of the radiation system.

In some embodiments, the at least one second detector is disposed in the second rotation portion without blocking the first imaging beam.

In some embodiments, the at least one second detector may be disposed in the first rotation portion. The second rotation portion may include at least one opening corresponding to the at least one second detector such that at least a portion of the at least one second imaging beam passes through the at least one opening and impinges on the at least one second detector.

In some embodiments, a first component of the first rotation portion and a second component of the second rotation portion may be located on a first plane.

In some embodiments, the treatment head may include a first portion and a second portion. The first component of the first rotation portion may include the first portion of the treatment head. The first portion of the treatment head may be configured to emit the treatment beam. The second component of the second rotation portion may include the second portion of the treatment. The second portion of the treatment head may include a collimation component configured to adjust a radiation range of the treatment beam.

In some embodiments, the first component of the first rotation portion may include a third detector configured to detect at least a portion of the treatment beam.

In some embodiments, the second component of the second rotation portion may include at least one of: a first imaging source of the one or more imaging sources that is configured to emit a first imaging beam towards the object; or a first detector of the at least one detector that is configured to detect at least a portion of the first imaging beam.

In some embodiments, at least one of a third component of the first rotation portion and a fourth component of the second rotation portion may be located on at least one second plane that is different from the first plane. The third component of the first rotation portion may be different from the first component. The fourth component of the second rotation portion may be different from the second component.

In some embodiments, the third component or the fourth component may include at least one of: a microwave device configured to facilitate a delivery of the treatment beam; an acceleration device configured to accelerate an electron beam to generate the treatment beam; a cooling device configured to cool at least one component of the treatment head; or a high-voltage device configured to facilitate a delivery of the one or more imaging beams.

In some embodiments, the first rotation portion may be outside the second rotation portion.

In some embodiments, the one or more imaging sources may include at least two imaging sources. The at least two imaging sources may be configured to emit at least two imaging beams of different energy levels.

In some embodiments, the at least one second imaging source may be disposed in the first rotation portion. The second rotation portion may include at least one opening corresponding to the at least one second imaging source such that at least a portion of the at least one second imaging beam passes through the at least one opening.

In some embodiments, the at least one second imaging source may be disposed in the second rotation portion.

In some embodiments, the first imaging source may include a computed tomography (CT) imaging source.

In some embodiments, the at least one second imaging source may include at least one digital radiography (DR) imaging source.

In some embodiments, a collimation component of the treatment head may be disposed in the first rotation portion.

In some embodiments, the second rotation portion may include an opening. The collimation component may be movable into the opening.

In some embodiments, the one or more components of the first rotation portion may include at least one of a treatment source, a jaw, a chamber, a primary collimator, or a secondary collimator of the treatment head.

In some embodiments, a collimation component of the treatment head may be disposed in the second rotation portion.

In some embodiments, the collimation component and the first imaging source may be arranged along a circumference of the second rotation portion.

In some embodiments, the collimation component and the first imaging source may be arranged parallel along a rotation axis of the second rotation portion.

In some embodiments, the first imaging source may be movable to a first position such that the first imaging source corresponds to a region of the object to be imaged during an imaging of the object. In some embodiments, the collimation component may be movable to a second position such that the collimation component corresponds to a region of the object to be treated during a radiation treatment of the object.

In some embodiments, a collimation component of the treatment head may be connected to the first rotation portion. The collimation component may be movable to a third position of the second rotation portion such that a position of the treatment beam corresponds to the third position of the collimation component.

In some embodiments, the first imaging source may rotate independently from a collimation component of the treatment head.

In some embodiments, the radiation system may also include at least one control component configured to cause the first rotation portion and the second rotation portion to rotate synchronously.

In some embodiments, the second rotation portion and the first rotation portion may be able to rotate independently.

In some embodiments, the radiation system may also include a locking component configured to lock the first rotation portion and the second rotation portion such that the first rotation portion and the second rotation portion rotate synchronously.

In some embodiments, the first rotation portion may be connected to a stationary portion of the radiation system via a bearing.

In some embodiments, the second rotation portion may be connected to the first rotation portion via a bearing.

In some embodiments, each of the first rotation portion and the second rotation portion may be connected to a stationary portion of the radiation system via a bearing, respectively.

In some embodiments, the radiation system may include a tilting component configured to facilitate a tilting of at least one of the first rotation portion, the second rotation portion, or a stationary portion of the radiation system.

In some embodiments, the tilting component may include a frame connected to the stationary portion. The stationary portion, the first rotation portion, and the second rotation portion may be tilted by moving the frame.

In some embodiments, the tilting component may also include a second frame connected to the stationary portion. The second frame may be configured to stabilize the stationary portion. The frame may be connected to the second frame.

According to another aspect of the present disclosure, a radiation system may be provided. The radiation system may include a first rotation portion; a second rotation portion; a treatment head comprising a first portion configured to emit a treatment beam towards an object and a second portion configured to adjust a radiation range of the treatment beam, the second portion of the treatment head being movable with respect to the first portion of the treatment head, and the first portion of the treatment head being disposed in the first rotation portion; one or more imaging sources, at least one of the one or more imaging sources being disposed in the second rotation portion; and at least one detector.

In some embodiments, the second rotation portion may include a space for accommodating the second portion of the treatment head.

In some embodiments, the second portion of the treatment head may be moveable into the space of the second rotation portion.

In some embodiments, the second rotation portion may be configured to rotate, at a first speed, independently from the first rotation portion during an imaging of the object.

In some embodiments, the second rotation portion and the first rotation portion may be configured to rotate synchronously at a second speed during a treatment of the object.

In some embodiments, the first speed may be higher than the second speed.

In some embodiments, the second portion of the treatment head may be disposed in the second rotation portion. The second portion of the treatment head and at least one of the one or more imaging sources may be arranged along a circumferential direction of the second rotation portion.

In some embodiments, the second portion of the treatment head and at least one of the one or more imaging sources may be arranged along a rotation axis of the second rotation portion. The second portion of the treatment head and at least one of the one or more imaging sources may be configured to move synchronously along the rotation axis.

In some embodiments, the second portion of the treatment head may be movable between the first rotation portion and the second portion and be connected to the first rotation portion.

In some embodiments, the second rotation portion may rotate independently from the second portion of the treatment head during an imaging of the object.

In some embodiments, each of the first rotation portion and the second rotation portion may be connected to a stationary portion via a bearing.

In some embodiments, the first rotation portion may be connected to a stationary portion via a first bearing. The second rotation portion may be connected to the first rotation portion via a second bearing.

In some embodiments, the radiation system may also include a tilting component configured to facilitate a tilting of at least one of the first rotation portion, the second rotation portion, or the stationary portion.

In some embodiments, the tilting component may include a frame configured to tilt the stationary portion so as to facilitate the tilting of the at least one of the first rotation portion, the second rotation portion, or the stationary portion.

In some embodiments, the first rotation portion may include an electronic portal imaging device (EPID) configured to detect at least a portion of the treatment beam.

In some embodiments, the one or more imaging sources may include a computed tomography (CT) imaging source or at least one digital radiography (DR) imaging source. The at least one detector may include a first detector corresponding to the CT imaging source or at least one second detector corresponding to the at least one DR imaging source.

In some embodiments, the at least one DR imaging source or the at least one second detector may be fixed at a fixed position of a room housing at least a portion of the radiation system.

In some embodiments, the at least one DR imaging source and at least one second detector may be disposed in at least one of the first rotation portion or the second rotation portion.

In some embodiments, at least one component of the first rotation portion and at least one component of the second rotation portion may be located on a same plane.

In some embodiments, the first rotation portion may be outside the second rotation portion.

In some embodiments, the radiation system may also include a locking component configured to lock the first rotation portion and the second rotation portion such that the first rotation portion and the second rotation portion rotate synchronously during a treatment of the object.

According to another aspect of the present disclosure, a system may be provided. The system may include: at least one storage device including a set of instructions; at least one processor in communication with the at least one storage device and a radiation system. The radiation system may include: a first rotation portion; a second rotation portion; a treatment head, at least a portion of the treatment head being disposed in the first rotation portion; one or more imaging sources, at least one of the one or more imaging sources being disposed in the second rotation portion; and at least one detector. When executing the set of instructions, the at least one processor may be configured to cause the system to perform operations including: causing the second rotation portion to rotate independently from the first rotation portion; generating an image by causing at least one of the one or more imaging sources to emit at least one imaging beam toward an object; causing a region of the object to be positioned in the radiation system based on the image; causing the first rotation portion and the second rotation portion to rotate synchronously; and causing the treatment head to emit a treatment beam to the region of the object.

In some embodiments, the at least one processor may also be configured to cause the system to perform the operations including: generating at least one second image by causing at least one of the one or more imaging sources to emit at least one imaging beam toward an object; and adjusting a delivery of the treatment beam or adjusting a position of the region of the object based on the at least one second image.

In some embodiments, the at least one of the one or more imaging sources may include a first imaging source. The first imaging source may rotate at a first speed when the second rotation portion rotates independently from the first rotation portion. The first imaging source may rotate at a second speed when the second rotation portion and the first rotation portion rotate synchronously. The first speed may be larger than the second speed.

In some embodiments, the first imaging source may include a CT imaging source.

In some embodiments, the at least one second image may be generated by performing a digital tomosynthesis (DTS) imaging of the object or by causing at least two of the one or more imaging sources to emit perpendicular imaging beams towards the object. The at least two of the one or more imaging sources may include multiple digital radiography (DR) imaging sources.

According to another aspect of the present disclosure, a method may be provided. The method may be implemented on a radiation system and a computing device having at least one processor, and at least one storage device. The radiation system may include: a first rotation portion; a second rotation portion; a treatment head, at least a portion of the treatment head being disposed in the first rotation portion; one or more imaging sources, at least one of the one or more imaging sources being disposed in the second rotation portion; and at least one detector. The method may include: causing the second rotation portion to rotate independently from the first rotation portion; generating an image by causing at least one of the one or more imaging sources to emit at least one imaging beam toward an object; causing a region of the object to be positioned in the radiation system based on the image; causing the first rotation portion and the second rotation portion to rotate synchronously; and causing the treatment head to emit a treatment beam to the region of the object.

In some embodiments, the method may also include: generating at least one second image by causing at least one of the one or more imaging sources to emit at least one imaging beam toward an object; and adjusting a delivery of the treatment beam or adjusting a position of the region of the object based on the at least one second image.

In some embodiments, the at least one of the one or more imaging sources may include a first imaging source. The first imaging source may rotate at a first speed when the second rotation portion rotates independently from the first rotation portion. The first imaging source may rotate at a second speed when the second rotation portion and the first rotation portion rotate synchronously. The first speed may be larger than the second speed.

In some embodiments, the first imaging source may include a CT imaging source.

In some embodiments, the at least one second image may be generated by performing a digital tomosynthesis (DTS) imaging of the object or by causing at least two of the one or more imaging sources to emit perpendicular imaging beams towards the object. The at least two of the one or more imaging sources may include multiple digital radiography (DR) imaging sources.

According to another aspect of the present disclosure, a non-transitory computer readable medium may be provided. The non-transitory computer readable medium may include instructions being executed by at least one processor, causing the at least one processor to implement a method on a radiation system. The radiation system may include: a first rotation portion; a second rotation portion; a treatment head, at least a portion of the treatment head being disposed in the first rotation portion; one or more imaging sources, at least one of the one or more imaging sources being disposed in the second rotation portion; and at least one detector. The method may include: causing the second rotation portion to rotate independently from the first rotation portion; generating an image by causing at least one of the one or more imaging sources to emit at least one imaging beam toward an object; causing a region of the object to be positioned in the radiation system based on the image; causing the first rotation portion and the second rotation portion to rotate synchronously; and causing the treatment head to emit a treatment beam to the region of the object.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
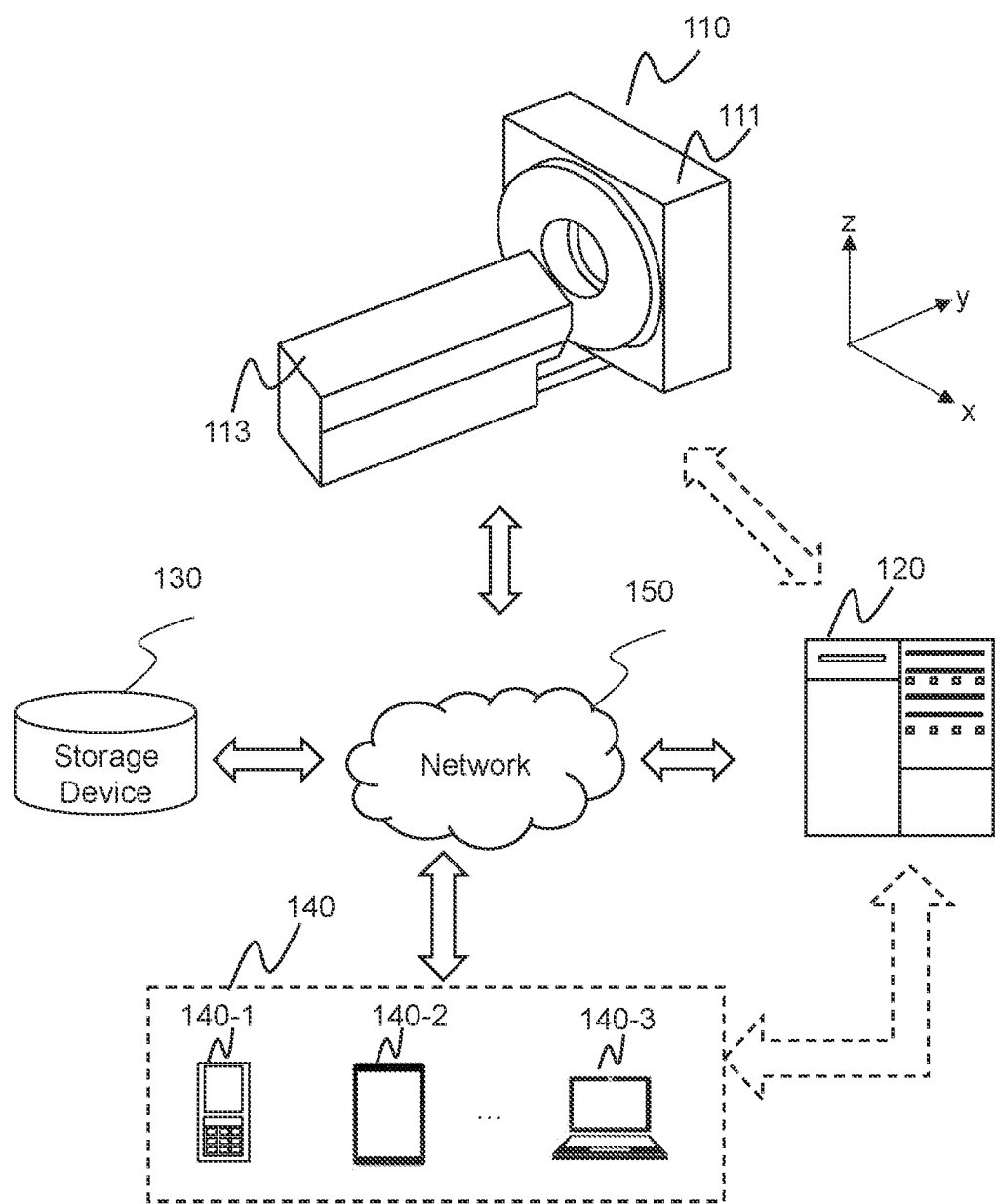
FIG. 1 is a schematic diagram illustrating an exemplary radiation system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

An aspect of the present disclosure relates to a radiation system. The radiation system may include a treatment head, one or more imaging sources, and at least one detector. In some embodiments, the one or more imaging sources and the at least one detector may constitute one or more imaging assemblies (or referred to as one or more imaging devices). Merely by way of example, the radiation system may include a CT imaging assembly and a DR imaging assembly, in which the CT imaging assembly may include at least one CT imaging source and at least one CT detector, and the DR imaging assembly may include at least one DR imaging sources and at least one DR detector. As described elsewhere in the present disclosure, in some embodiments, the CT imaging assembly and the DR assembly may share a detector; in some embodiments, the CT imaging assembly and the DR assembly may each have their own one or more detectors. The treatment head may be configured to deliver a treatment beam towards an object. The one or more imaging sources may be configured to deliver one or more imaging beams towards the object. The at least one detector may be configured to detect at least a portion of the one or more imaging beams. In some embodiments, at least a portion of the treatment head (e.g., a first head portion of the treatment head, the whole treatment head) may be disposed in a first rotation portion of the radiation system. In some embodiments, at least a portion of the treatment head (e.g., a second head portion of the treatment head) may be disposed in a second rotation portion of the radiation system. In some embodiments, at least one of the one or more imaging sources and/or at least one of the at least one detector may be disposed in the second rotation portion. In some embodiments, at least one of the one or more imaging sources and/or at least one of the at least one detector may be disposed in the first rotation portion.

In some embodiments, the first rotation portion and the second rotation portion may be configured to have two rotation modes including a first rotation mode and a second rotation mode. The first rotation portion and the second rotation portion may rotate independently from each other under the first rotation mode. The first rotation portion and the second rotation portion may rotate synchronously under the second rotation mode.

During the emission of the at least one imaging beam, the second rotation portion may be controlled to rotate independently from the first rotation portion. Thus, the at least one of the one or more imaging sources may rotate without the influence of the first rotation portion (e.g., a weight of the first rotation portion, a rotation speed of the first rotation portion). The at least one of the one or more imaging sources may rotate at a relatively high speed (e.g., smaller than 0.3 seconds per revolution, smaller than 0.5 seconds per revolution), thereby increasing an imaging speed, reducing imaging artifacts, and/or improving an imaging quality.

In some embodiments, after the imaging of the object is completed, the treatment head may be caused to emit the treatment beam to perform a radiation treatment of a region of the object. In some embodiments, portions of the treatment head may be located on the first rotation portion and the second rotation portion. For instance, a collimation component of the treatment head is located on the second rotation portion, while the treatment source is located on the first rotation portion. During the radiation treatment of the region, the second rotation portion and the first rotation portion may be controlled to rotate synchronously such that portions of the treatment head may collectively operate to emit the treatment beam. By positioning the collimation component on the second rotation portion that has a smaller diameter than the first rotation portion, a resolution of a treatment region formed using the collimation component on the object may be improved. Additionally or alternatively, a radius of the bore of the radiation system may be set sufficiently large to facilitate the positioning of the object within the bore for imaging (and/or radiation treatment), and/or make the patient more comfortable and/or less stressful/nervous when placed in the bore. To achieve a desirable quality for imaging, the distance between the object, or a portion thereof (e.g., the region of the object to be imaged), may need to be small, e.g., below a threshold. Accordingly, to accommodate both considerations, at least one of the one or more imaging sources may be set closer to the isocenter of the imaging assembly including the at least one of the one or more imaging sources.

In some embodiments, at least one image (e.g., a three-dimensional image) may be generated by causing at least one of the one or more imaging sources (e.g., a computed tomography (CT) imaging source) in the second rotation portion to emit at least one imaging beam towards a region (e.g., a region to be treated) (also referred to as a region of interest (ROI) of the object. The at least one image may be used to guide the positioning of the object and/or adjust a treatment plan of the object.

FIG. 1 is a schematic diagram illustrating an exemplary radiation system according to some embodiments of the present disclosure. In some embodiments, the radiation system 100 may be configured to provide radiation therapy (also referred to as a radiation treatment) (e.g., stereotactic radiosurgery and/or precision radiotherapy) for lesions, tumors, and conditions anywhere in a patient where radiation treatment is indicated. In some embodiments, the radiation system 100 may include a treatment plan system (TPS), an image-guided radiotherapy (IGRT) system, etc.

As illustrated in FIG. 1, the radiation system 100 may include a medical device 110, a processing device 120, a storage device 130, one or more terminals 140, and a network 150. The components in the radiation system 100 may be connected in one or more of various ways. Merely by way of example, the medical device 110 may be connected to the processing device 120 through the network 150. As another example, the medical device 110 may be connected to the processing device 120 directly as indicated by the bi-directional arrow in dotted lines linking the medical device 110 and the processing device 120. As a further example, the storage device 130 may be connected to the processing device 120 directly or through the network 150. As still a further example, the terminal 140 may be connected to the processing device 120 directly (as indicated by the bi-directional arrow in dotted lines linking the terminal 140 and the processing device 120) or through the network 150.

In some embodiments, the radiation system 100 may perform image-guided radiation therapy (IGRT) that monitors, using X-ray imaging, a target volume (also referred to as a target region, a region, e.g., a tumor, a lesion, etc.) to be treated inside an object (e.g., a patient). In this case, the medical device 110 may include a treatment assembly (also referred to as a treatment device) and/or an imaging assembly (also referred to as an imaging device). The treatment assembly may be configured to deliver a treatment beam to the target volume to perform a radiotherapy on the target volume. The imaging assembly may be configured to perform imaging (e.g., two-dimensional (2D) imaging, three-dimensional (3D) imaging, or four-dimensional (4D) imaging) on the target volume and/or normal tissue surrounding the target volume (also referred to as "organ at risk") before, after, or while the radiotherapy is performed. In this way, the anatomy, as well as the motion or deformation, of the target volume can be detected, and the patient's position and/or the treatment beam can be adjusted for more precise radiation dose delivery to the target volume.

In the present disclosure, the x-axis, the y-axis, and the z-axis shown in FIG. 1 may form an orthogonal coordinate system. The x-axis and the y-axis shown in FIG. 1 may be horizontal, and the z-axis may be vertical. As illustrated, the positive x-direction along the x-axis may be from the left side to the right side of the medical device 110 seen from the direction facing the front of the medical device 110; the positive z-direction along the z-axis shown in FIG. 1 may be from the lower part to the upper part of the medical device 110; the positive y-direction along the y-axis shown in FIG. 1 may refer to a direction in which an object is moved into a bore of the medical device 110.

In some embodiments, the medical device 110 may include a gantry 111 (e.g., an O-shaped gantry) and a patient support 113. In some embodiments, the gantry 111 may be configured to support at least one component of the imaging assembly and/or at least one component of the treatment assembly, for example, one or more of a treatment head, one or more imaging sources, at least one detector, etc. The gantry 111 may be configured to rotate around an object (e.g., a patient, or a portion thereof) that is moved into or located within a field of view (FOV) (e.g., a region covered by at least one radiation beam emitted from at least one of the treatment head or the one or more imaging sources) of the medical device 110. Merely by way of example, the medical device 110 may include a computed tomography (CT) imaging device, a digital radiology (DR) imaging device, a surface guided radiation therapy device, an ultrasonic imaging device, an X-ray device, a magnetic resonance (MR) imaging device, a positron emission tomography (PET) imaging device, a single photon emission computed tomography (SPECT) imaging device, a digital subtraction angiography (DSA) imaging device, or the like, or any combination thereof.

In some embodiments, the treatment head may rotate about an axis of the gantry 111 (e.g., parallel to the y-axis in FIG. 1) and within a first rotation plane (or referred to as a first rotation ring or simply a first ring). A center point of the first rotation plane may be referred to as an isocenter of the treatment assembly. The axis of the gantry 111 may pass through the isocenter of the treatment assembly and be perpendicular to the first rotation plane.

In some embodiments, at least one of the one or more imaging sources may rotate about the axis of the gantry 111 (e.g., parallel to the y-axis in FIG. 1) and within a second rotation plane (or referred to as a second rotation ring or simply a second ring). A center point of the second rotation plane may be referred to as an isocenter of the imaging assembly. The axis of the gantry 111 may pass through the isocenter of the imaging assembly and be perpendicular to the second rotation plane.

In some embodiments, the patient support 113 may be configured to support the object. The patient support 113 may have multiple (e.g., 6) degrees of freedom, for example, three translational degrees of freedom along three coordinate directions (i.e., x-direction, y-direction, and z-direction) and three rotational degrees of freedom around the three coordinate directions. Accordingly, the patient support 113 may move the object along a direction of the 3D coordinate system. Merely by way of example, the patient support 113 may move the object into the FOV of the medical device 110 along the y-direction in FIG. 1.

In some embodiments, the object may be biological or non-biological. Merely by way of example, the object may include a patient, a man-made object, etc. As another example, the object may include a specific portion, organ, and/or tissue of the patient. For example, the object may include head, brain, neck, body, shoulder, arm, thorax, cardiac, stomach, blood vessel, soft tissue, knee, feet, or the like, or any combination thereof. In the present disclosure, "subject" and "object" are used interchangeably.

In some embodiments, the imaging assembly may include one or more imaging sources. The one or more imaging sources may be configured to deliver one or more imaging beams toward the object (e.g., a region of interest (ROI) of the object). Each of the one or more imaging sources may be configured to deliver at least one imaging beam. In some embodiments, the first imaging source may be configured to emit a first imaging beam towards the object. The at least one second imaging source may be configured to emit at least one second imaging beam towards the object. In some embodiments, the one or more imaging sources may include a first imaging source (e.g., a computed tomography (CT) imaging source) of a first type and/or at least one second imaging source (e.g., at least one digital radiography (DR) imaging source) of a second type. For example, the one or more imaging sources may include the first imaging source of the first type. As another example, the one or more imaging sources may include the at least one second imaging source of the second type. As a further example, the one or more imaging sources may include the first imaging source of the first type and the at least one second imaging source of the second type.

In some embodiments, the first type may be different from the second type. In some embodiments, the first type may be the same as the second type. In some embodiments, the at least one second imaging source may include two or more second imaging sources. The two or more second imaging sources may be of a same type, e.g., DR imaging sources. In some embodiments, the two or more second imaging sources may be of different types, e.g., at least one DR imaging source and at least one imaging source of other types (e.g., an infrared source of an infrared imaging device, a microwave source of a microwave imaging device, an imaging radar, an X-ray generator, an ultrasound generator of an ultrasonic imaging device, a magnetic field generator (e.g., a coil) of an MR imaging device).

In some embodiments, the imaging assembly may include at least one detector. In some embodiments, the at least one detector may be set opposite to the one or more imaging sources respectively. In some embodiments, the at least one detector may be configured to detect at least a portion of the one or more imaging beams. In some embodiments, each of the first imaging source and the at least one second imaging source may correspond to one of the at least one detector; that is, the detector may be configured to only detect at least a portion of an imaging beam emitted by the imaging source. In some embodiments, at least two of the first imaging source and the at least one second imaging source may share one of the at least one detector (e.g., a first detector described below) (e.g., a curvilinear detector); that is, the detector may be configured to detect at least two imaging beams emitted by the at least two different imaging sources. The detected at least two imaging beams may be emitted by different imaging sources of the plurality of imaging sources.

In some embodiments, the at least one detector may include a first detector and/or at least one second detector. The first detector (e.g., a curvilinear detector, a flat panel detector) may be configured to detect at least a portion of the first imaging beam. The at least one second detector (e.g., at least one flat panel detector) may be configured to detect at least a portion of the at least one second imaging beam.

In some embodiments, the imaging assembly may also include a tube, a high-voltage device, etc. The tube and/or the high-voltage device may be configured to facilitate a delivery of the one or more imaging beams. For example, the tube may be configured to generate the one or more imaging beams. The high-voltage device may accelerate an electron beam to generate the one or more imaging beams.

In some embodiment, the treatment assembly may include a treatment head. The treatment head may be configured to deliver a treatment beam toward the object to perform a radiation treatment toward a region inside the object and/or perform imaging on a region of interest (ROI) (e.g., including the target volume and/or organs at risk (OARs)) of the object. In some embodiments, the treatment head may include a first portion (also referred to as a first head portion) and a second portion (also referred to as a second head portion). For example, the first head portion and the second head portion may constitute the whole treatment head.

In some embodiments, the treatment assembly may include a third detector (e.g., an electronic portal imaging device (EPID)) configured to detect at least a portion of the treatment beam. In some embodiments, the third detector may be configured to detect kV beams and also MV beams. In some embodiments, the third detector may be configured to detect kV beams only or MV beams only.

In some embodiments, the first head portion may include one or more of a treatment source (e.g., an X-ray target), a microwave device, an acceleration device (e.g., an acceleration tube), a first cooling device, a primary collimator, a filter (e.g., a flattening filter), a chamber, etc. The acceleration device may be configured to accelerate an electron beam to generate the treatment beam. The microwave device may be configured to facilitate the delivery of the treatment beam. For example, the microwave device may generate an electromagnetic field for accelerating the electron beam to a relatively high energy. The first cooling device may be configured to cool at least one component of the treatment head (e.g., the microwave device, the acceleration device). The primary collimator may be configured to adjust a radiation range of the treatment beam. The filter may be configured to generate a filtered treatment beam by adjusting an energy distribution of the treatment beam. The chamber may be configured to ionize gas in the chamber to detect at least one parameter (e.g., an intensity, a flatness, a symmetry) of the treatment beam. In some embodiments, the acceleration device may include an acceleration tube of particles including, for example, photons, electrons, protons, or heavy ions, etc. In some embodiments, the treatment beam may include a relatively high energy beam (e.g., an MV beam). In some embodiments, the treatment beam may include a fan beam, a cone beam, or a tetrahedron beam.

In some embodiments, the second head portion, also referred to as a collimation component, may include, e.g., one or more of a jaw, a secondary collimator (e.g., a multi-leaf collimator (MLC)), filter of the primary collimator, the jaw, or leaves of the MLC.

In some embodiments, the medical device 110 may include a first rotation portion and a second rotation portion. At least one component of the imaging assembly and/or at least one component of the treatment assembly (collectively referred to as a first component assembly) may be disposed in the first rotation portion. In some embodiments, the first component assembly may include at least a portion of the treatment head, the third detector, the at least one second imaging source, the at least one second detector, the tube, the high-voltage device, or the like, or any combination thereof. Merely by way of example, the at least a portion of the treatment head may include the first head portion. As another example, the at least a portion of the treatment head may include the first head portion and the second head portion.

Figure 7:
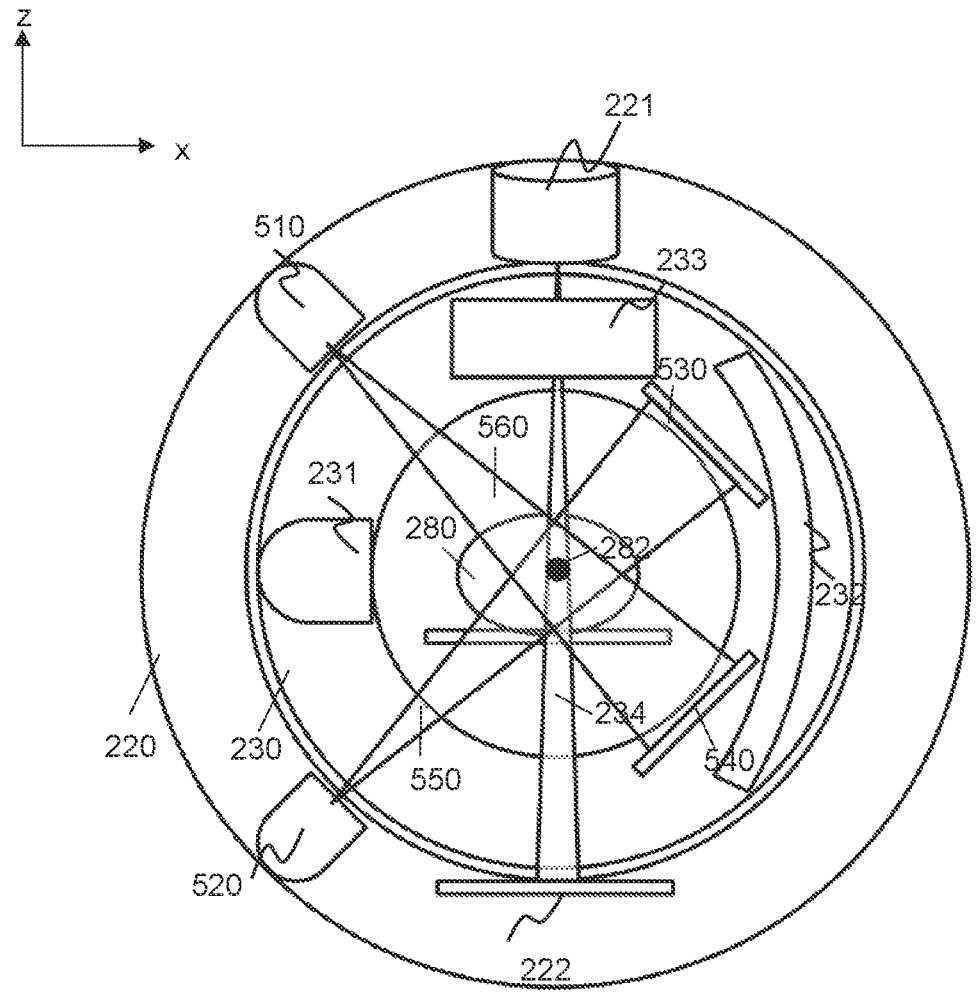
FIG. 7 is a section view illustrating an exemplary medical device according to some embodiments of the present disclosure.

For example, the at least a portion of the treatment head may be disposed in the first rotation portion. As another example, the at least a portion of the treatment head and the third detector may be disposed in the first rotation component (e.g., as shown in FIGS. 2-5). As a further example, the at least a portion of the treatment head and at least one of the at least one second imaging source may be disposed in the first rotation portion (e.g., as shown in FIG. 7). As still a further example, the at least a portion of the treatment head and at least one of the at least one second detector may be disposed in the first rotation portion.

In some embodiments, at least one component of the imaging assembly and/or at least one component of the treatment assembly (collectively referred to as a second component assembly) may be disposed in the second rotation portion. In some embodiments, the second component assembly may include at least one of the one or more imaging sources, at least one of the at least one detector, the collimation component, the third detector, the tube, the high-voltage device, or the like, or any combination thereof.

Figure 2:
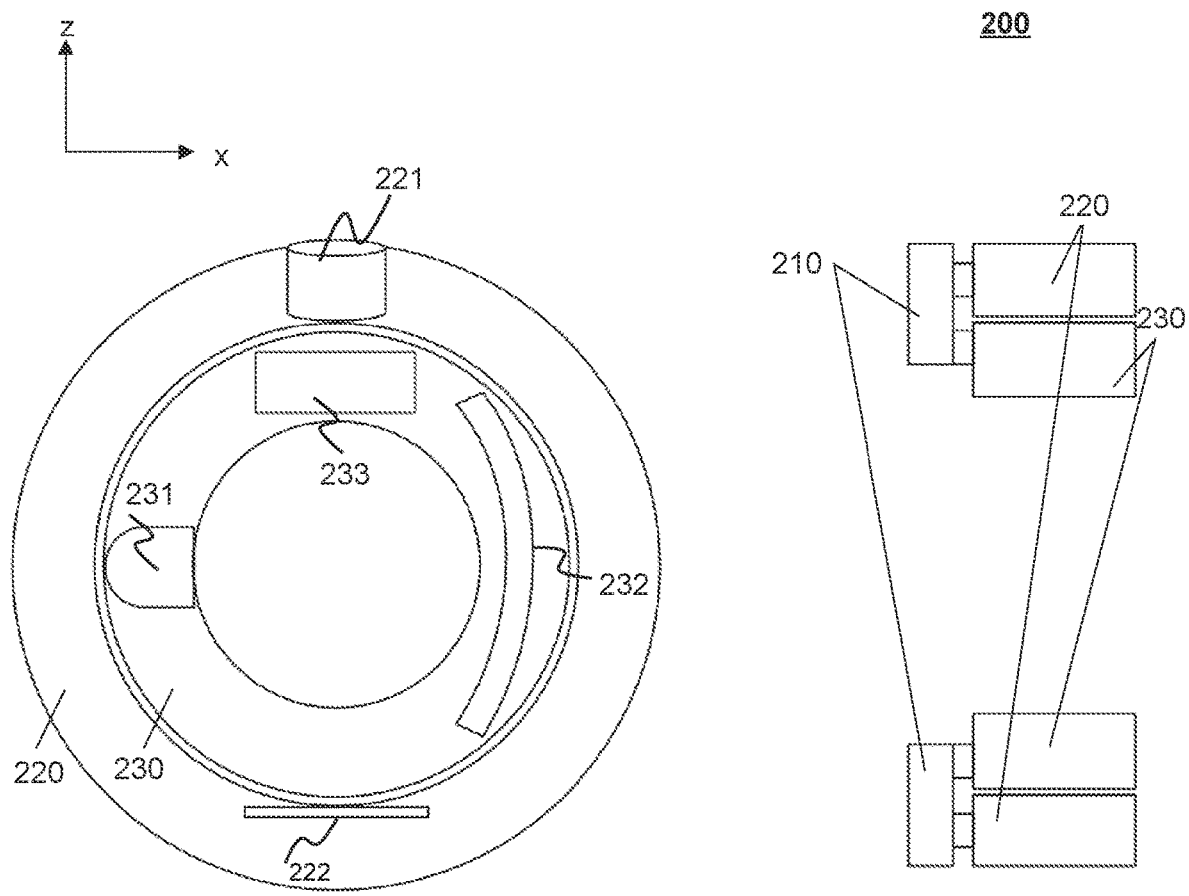
FIG. 2 is a section view illustrating an exemplary medical device according to some embodiments of the present disclosure.
Figure 3:
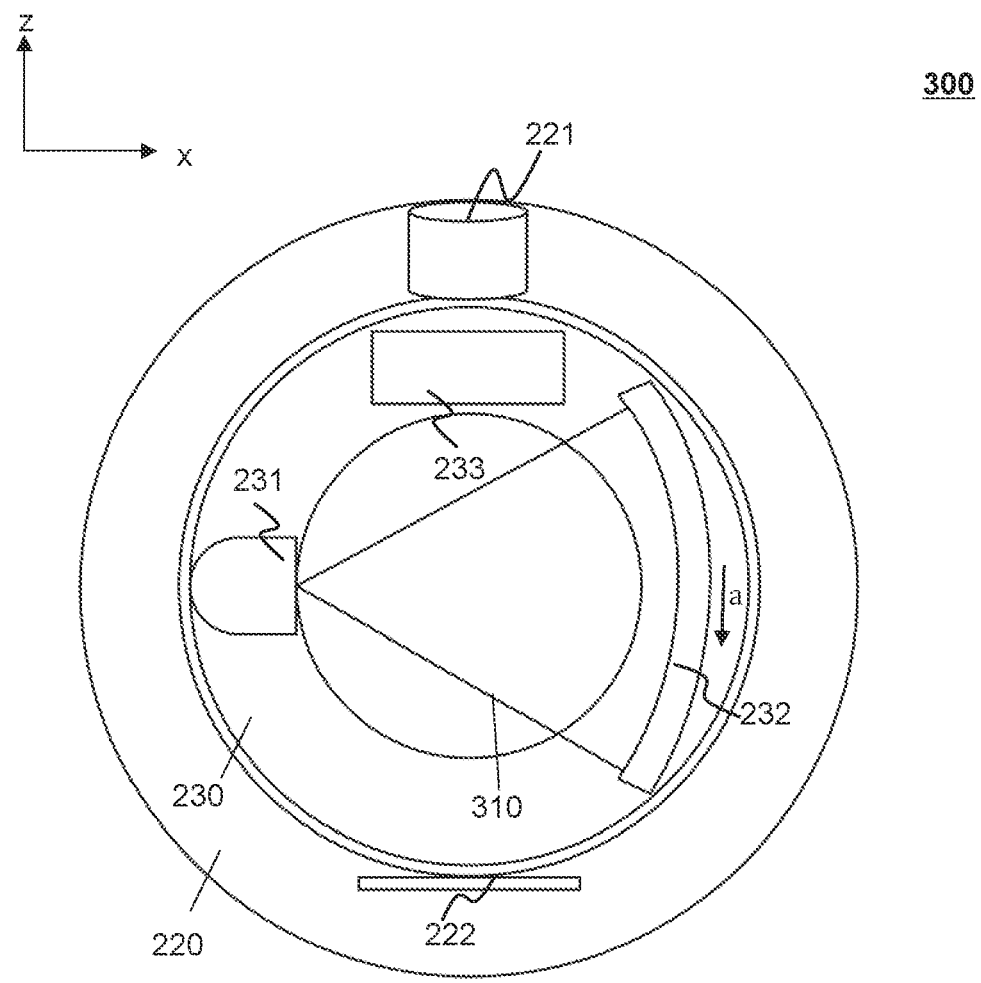
FIG. 3 is a section view illustrating an exemplary medical device according to some embodiments of the present disclosure.
Figure 4:
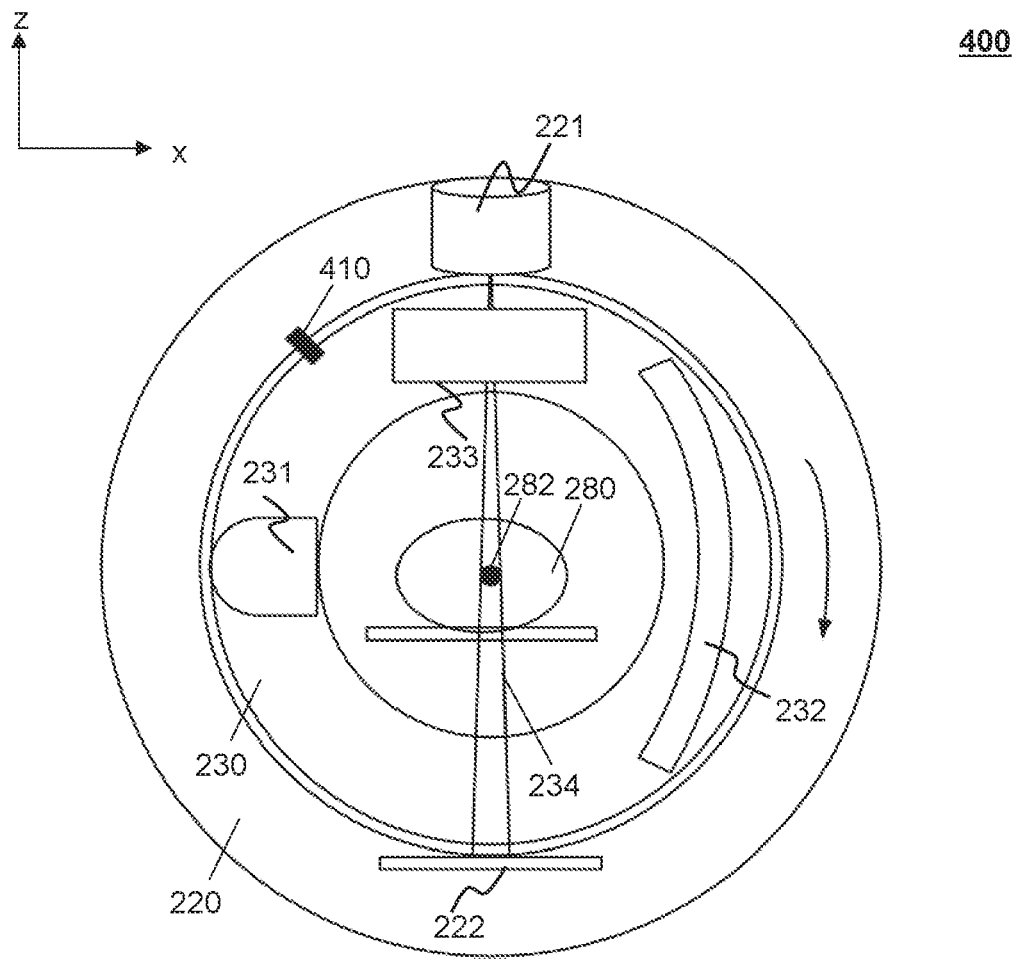
FIG. 4 is a section view illustrating an exemplary medical device according to some embodiments of the present disclosure.
Figure 5:
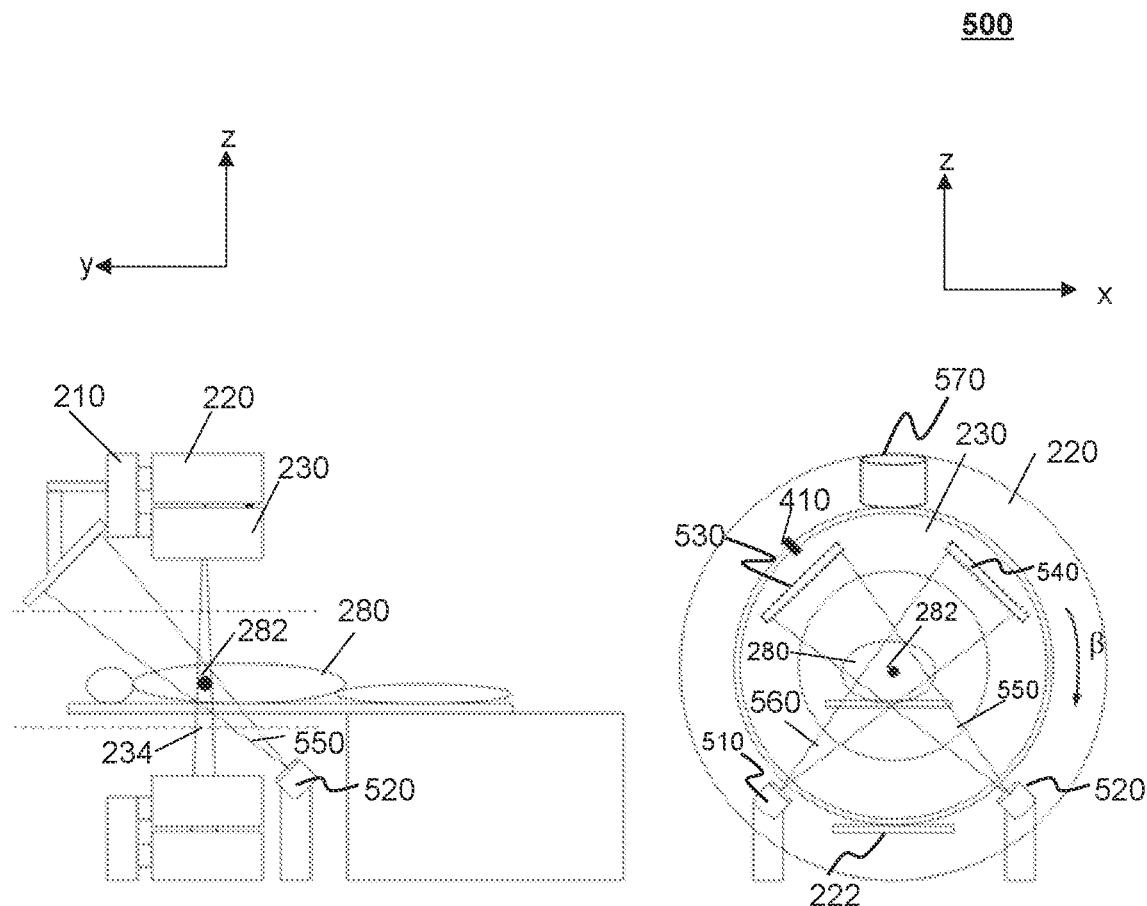
FIG. 5 is a section view illustrating an exemplary medical device according to some embodiments of the present disclosure.
Figure 6:
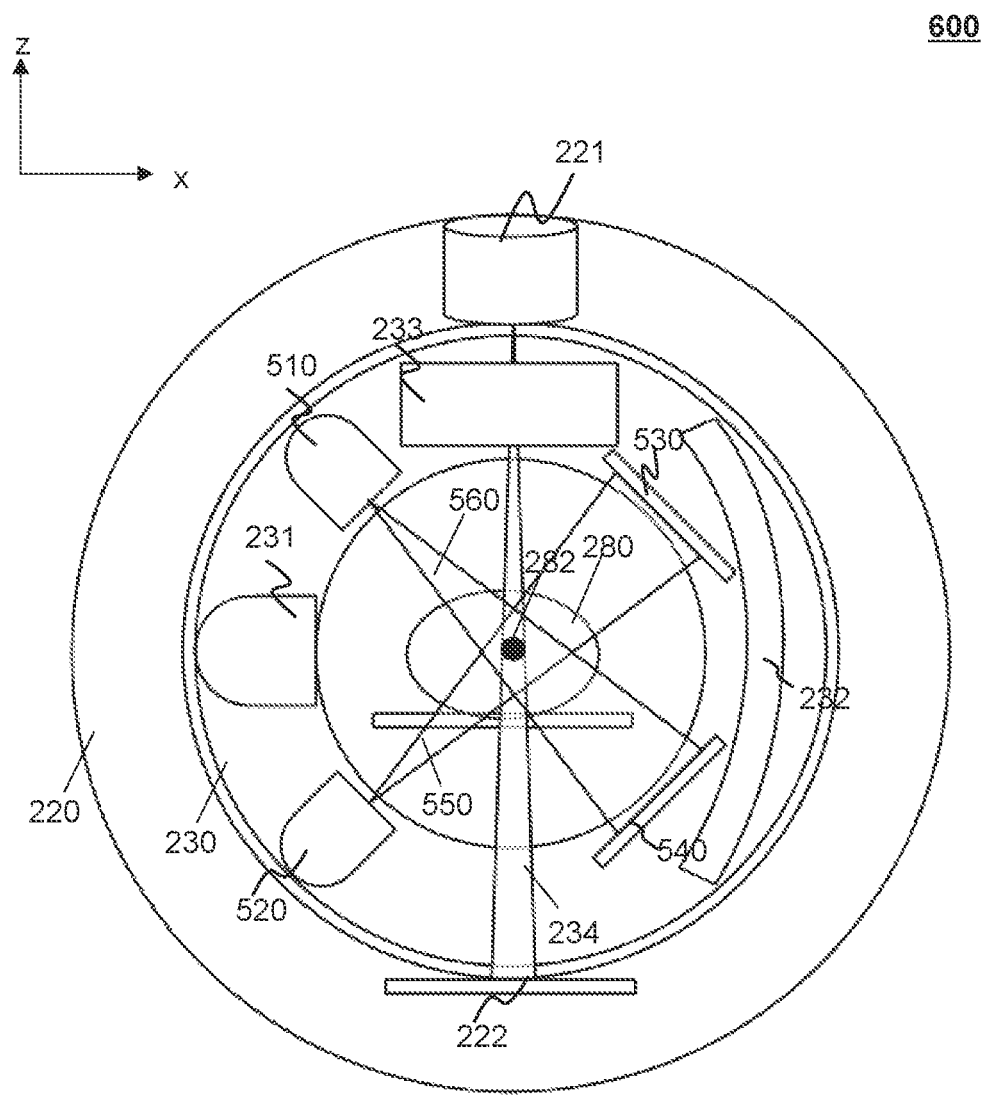
FIG. 6 is a section view illustrating an exemplary medical device according to some embodiments of the present disclosure.
Figure 9:
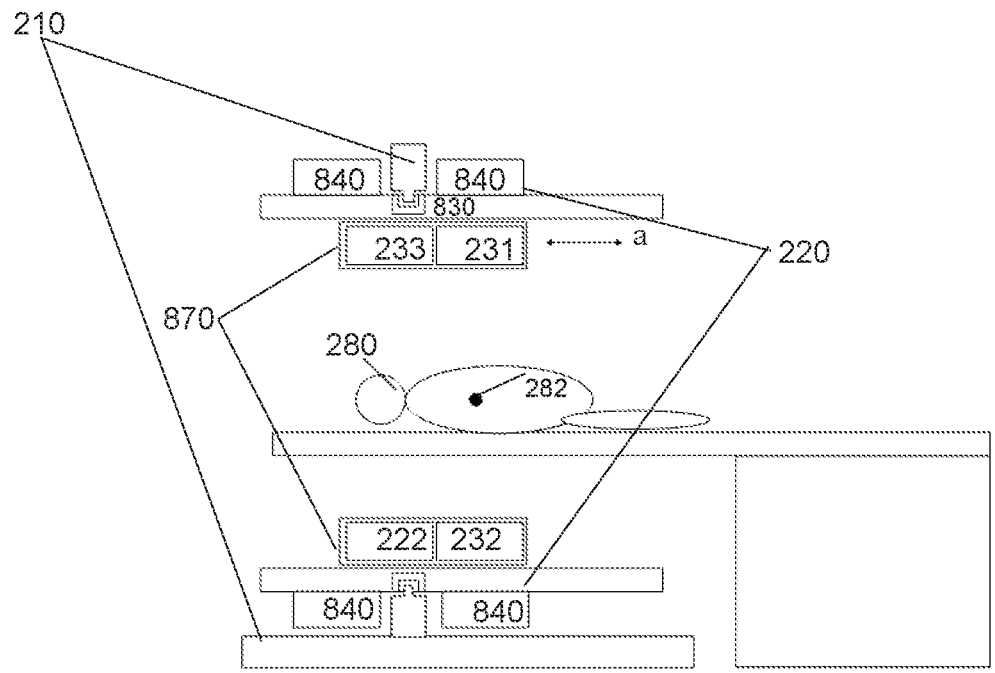
FIG. 9 and FIG. 10 are section views illustrating an exemplary medical device according to some embodiments of the present disclosure.
Figure 10:
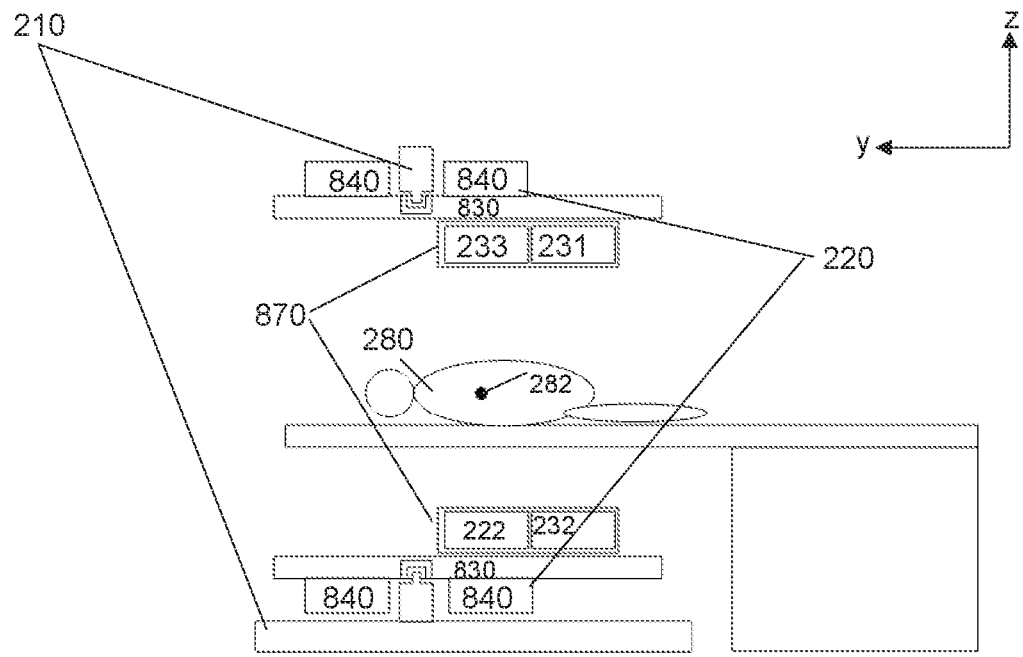
Figure 11:
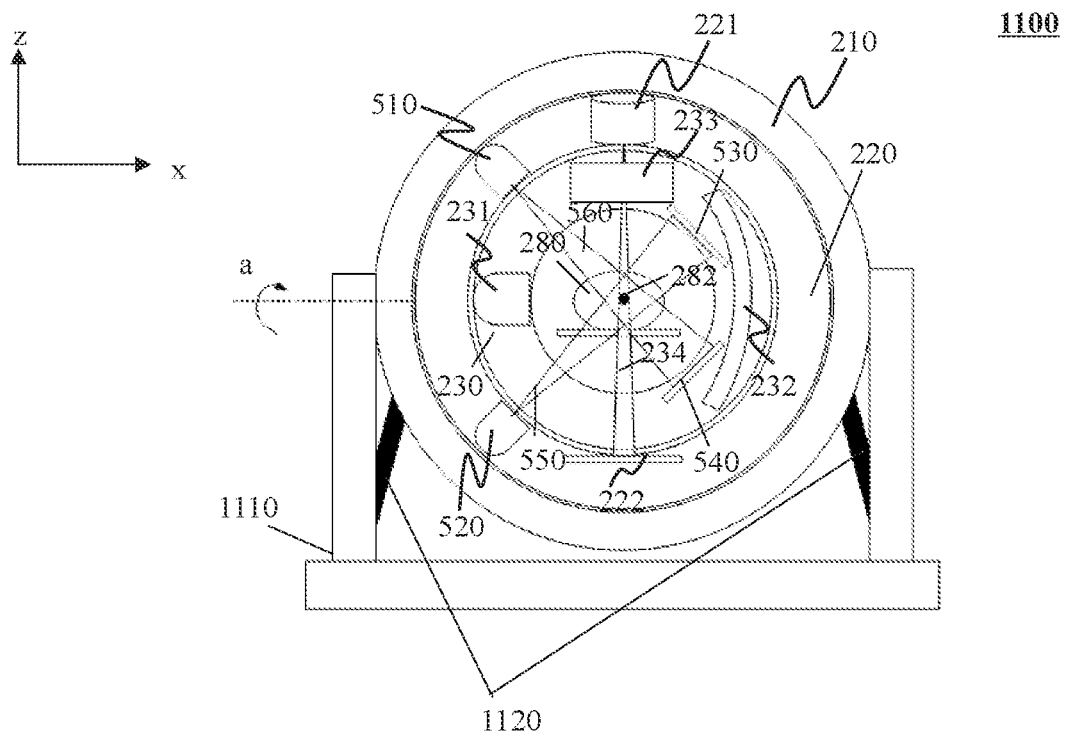
FIG. 11 and FIG. 12 are section views illustrating an exemplary medical device according to some embodiments of the present disclosure.

For example, the first imaging source may be disposed in the second rotation portion. As another example, the first detector may be disposed in the second rotation portion. As a further example, the first detector and the first imaging source may be disposed in the second rotation portion (e.g., as shown in FIG. 5). As still a further example, the first imaging source and at least one of the at least one second imaging source may be disposed in the second rotation portion. As still a further example, at least one of the at least one second detector may be disposed in the second rotation portion. As still a further example, the first detector and at least one of the at least one second detector may be disposed in the second rotation portion. As still a further example, the collimation component may be disposed in the second rotation portion. As still a further example, the first imaging source, the first detector, and the collimation component may be disposed in the second rotation portion (e.g., as shown in FIGS. 2-4). As still a further example, the first imaging source, the first detector, and at least one of the at least one second detector may be disposed in the second rotation portion (e.g., as shown in FIG. 6 or FIG. 7). As still a further example, the collimation component, the first imaging source, at least one of the at least one second imaging source, and at least one of the second detector or the first detector may be disposed in the second rotation portion (e.g., as shown in FIG. 6). As still a further example, the first imaging source, the collimation component, the first detector, and the third detector may be disposed in the second rotation portion (e.g., as shown in FIG. 9 or FIG. 10). As still a further example, the collimation component, the first imaging source, the third detector, at least one of the at least one second detector or the first detector may be disposed in the second rotation portion (e.g., as shown in FIG. 7 or FIG. 11).

In some embodiments, a second cooling device may be disposed in the second rotation portion and configured to cool at least one component (e.g., the high-voltage device, the tube) of the second rotation component. In some embodiments, a counterweight component may be disposed in the first rotation portion and/or the second rotation portion. The counterweight component may be configured to adjust a weight distribution of the first and/or second rotation portion such that the first and/or second rotation portion may be balanced during rotation.

In some embodiments, the first rotation portion may include a first rotor. The first rotor may be configured to facilitate a rotation of the first component assembly. It should be noted that the first rotation portion may be considered as the first rotor, and the first component assembly may be disposed in the first rotor or the first rotation portion. In some embodiments, the second rotation portion may include a second rotor. The second rotor may be configured to facilitate a rotation of the second component assembly. It should be noted that the second rotation portion may be considered as the second rotor, and the second component assembly may be disposed in the second rotor or the first rotation portion.

In some embodiments, the first imaging source and the first detector may be disposed in and rotatable with the second rotation portion. The first imaging source and/or the first detector may rotate to acquire an imaging dataset of the object from different views. In such cases, there may be one first imaging source and one first detector of the medical device 110. The first imaging source and the first detector may be disposed in the second rotor and rotatable with the second rotor. In some embodiments, the collimation component may be stationary with respect to the first imaging source. Accordingly, the first imaging source and the first detector may rotate independently from the collimation component, thereby reducing a load of the second rotation portion that carries the first imaging source and the first detector during the rotation, such that the first imaging source may rotate at a relatively high speed. The first imaging source and the first detector may be fixed, via one or more first bearings, on a support component configured to support both the collimation component and the first imaging source. Additionally or alternatively, the second rotor may be fixed on the support component via the one or more first bearings. In some embodiments, the support component may also be moved. See, e.g., FIG. 9 in which the support component 870 is moveable along a direction a.

In some embodiments, the collimation component may be rotatable with the first imaging source. The first imaging source, the first detector, and the collimation component may be disposed in the second rotor and rotatable with the second rotor. The first imaging source, the first detector, and the collimation component may be fixed on the support component via one or more second bearings. Additionally or alternatively, the second rotor may be fixed on the support component via the one or more second bearings.

In some embodiments, the second rotor may be unnecessary, and the first imaging source and the first detector may be stationary, e.g., with respect to a fixed component (e.g., the floor, a wall) of a room housing at least a portion of the radiation system 100. There may be multiple first imaging sources and/or multiple first detectors of the medical device 110 such that the object may be imaged from different views and imaging datasets of such different views may be acquired. For example, the imaging dataset of the object may be acquired by controlling the multiple first imaging sources to sequentially emit imaging beams.

In some embodiments, the first rotation portion and the second rotation portion may be configured to have two rotation modes including a first rotation mode and a second rotation mode. The first rotation portion and the second rotation portion may rotate independently from each other under the first rotation mode. The first rotation portion and the second rotation portion may rotate synchronously under the second rotation mode.

In some embodiments, the second rotation portion may be configured to rotate independently from the first rotation portion. The first rotation portion may rotate along a first ring (also referred to as a first rotation plane, a first rotation ring, or a treatment plane). The second rotation portion may rotate along a second ring (also referred to as a second rotation ring, a second rotation plane, or an imaging plane). The first ring and the second ring may be different. In some embodiments, both the first ring and the second ring may be perpendicular to an axis of the gantry 111 (e.g., the y-axis in FIG. 1), e.g., two parallel rings in the xz-plane. An axis of the first ring and an axis of the second ring may pass through an isocenter of the medical device 110 (e.g., the isocenter of the imaging assembly, the isocenter of the treatment assembly), respectively. In some embodiments, the first ring and the second ring may be concentric. A radius of the first ring may be larger than a radius of the second ring.

In some embodiments, the medical device 110 may include a stationary portion connected to the first rotation portion and the second rotation portion. The stationary portion may be configured to support at least one component of the radiation system 100, supply power to at least one component of the radiation system, transmit a signal (e.g., a control signal, a data signal) to at least one component of the radiation system 100, etc. In some embodiments, the first rotation portion, the second rotation portion, and the stationary portion may be integrated on the gantry 111 of the medical device 110. It is understood that when a component is referred to as being "integrated in" another component used herein, it may be directly on, connected or coupled to, or communicate with the another component, or an intervening component may be present, unless the context clearly indicates otherwise.

In some embodiments, each of the first rotation portion and the second rotation portion may be connected to the stationary portion via a bearing, respectively. In some embodiments, the first rotation portion (e.g., the first rotor) may be connected to the stationary portion via a first bearing. The second rotation portion (e.g., the second rotor) may be connected to the stationary portion via a second bearing. In some embodiments, when the first rotation portion and the second rotation portion both rotate but independently, a position (e.g., in a radial direction) of the second rotation portion relative to a position (e.g., in a radial direction) of the first rotation portion may be unchanged or change slightly. As used herein, "changing slightly" indicates that the change (e.g., the change in the position of the first rotation portion relative to the position of the second rotation portion) is below a threshold, e.g., 10%, 8%, 5%, etc. In some embodiments, the position of the second rotation portion relative to the position of the first rotation portion may be unchanged or change slightly by fixing the first rotation portion on the second rotor when the first rotation portion or the second rotation portion rotates. Regardless of how the first rotation portion and the second rotation portion are arranged with respect to each other, a rotation angle of the first rotation portion and a rotation angle of the second rotation portion may be (substantially) the same. As used herein, "substantially" indicates that the deviation (e.g., the deviation from the rotation angle of the first rotation portion and the rotation angle of the second rotation portion being "the same") is below a threshold, e.g., 10%, 8%, 5%, etc.

In some embodiments, the first rotation portion (e.g., the first rotor) and the stationary portion may also be connected via a first slip ring. The first slip ring may be configured to supply power to the first component assembly of the first rotation portion and/or transmit a signal (e.g., a control signal, an electric signal) to at least one component of the radiation system 100, etc. In some embodiments, a position of the first slip ring may be set according to practical demands. For example, a portion of the first slip ring may be disposed in the stationary portion, and a portion of the first slip ring may be disposed in the first rotation portion.

In some embodiments, the first rotation portion and the second rotation portion may be connected via a second slip ring. The second slip ring may be configured to supply power to the second component assembly of the second rotation portion. A position of the second slip ring may be set according to practical demands. For example, a portion of the second slip ring may be disposed in the stationary portion, and a portion of the second slip ring may be disposed in the second rotation portion.

In some embodiments, the at least one second detector may be fixed at a fixed position of a room housing at least a portion of the radiation system 100 (e.g., on a wall, on the floor), that is, the at least one second detector is not rotatable with the first imaging source. In some embodiments, the at least one second detector may be disposed in the second rotation portion. Before the treatment head is caused to emit a treatment beam towards a region (e.g., a region to be treated) (also referred to as a region of interest (ROI) of the object to perform a radiation treatment of the region, the first imaging source may be caused to emit an imaging beam of a first fan angle to the region to generate an image (e.g., a 3D image) of the object. The image may be used to guide a positioning of the region and/or adjust a treatment plan of the object. More descriptions of guiding the positioning of the region and/or adjusting the treatment plan of the object may be found elsewhere in the present disclosure. See. e.g., FIG. 17, 18, or the descriptions thereof.

In some embodiments, the at least one second detector may be configured to be set at a first position (e.g., along an axial direction or a circumferential direction of the gantry 111) (e.g., a position of a plane of the treatment beam) to prevent the at least one second detector from blocking a pathway of at least a portion of the imaging beam of the first fan angle. In some embodiments, the at least one second detector may be movable to the first position.

In some embodiments, during the radiation treatment of the region, the at least one second imaging source may be caused to emit at least one second imaging beam towards the object to perform an imaging of the object. In some embodiments, before the emission of the at least one second imaging beam, the at least one second detector may be moved to a second position such that at least a portion of the at least one second imaging beam may be received by the at least one second detector. Information acquired in the imaging process may be used to monitor the radiation treatment. More descriptions of monitoring the radiation treatment may be found elsewhere in the present disclosure. See. e.g., FIG. 17, 18, or the descriptions thereof.

In some embodiments, during the radiation treatment of the region, the first imaging source and the at least one second imaging source may be caused to emit an imaging beam of a second fan angle and at least one second imaging beam, respectively to perform the imaging of the object. Before the emission of the imaging beam of the second fan angle and the at least one second imaging beam, the at least one second detector may be moved to a third position such that at least a portion of the at least one second imaging beam may be received by the at least one second detector and at least a portion of the imaging beam of the second fan angle may be received by the first detector. In some embodiments, the first fan angle may be larger than the second fan angle. In some embodiments, the at least one second detector may be positioned in the second rotation portion such that the at least one second detector does not block at least a portion of the imaging beam emitted by the first imaging source (thereby obviating the need to move the at least one second detector to allow the passage of at least a portion of the imaging beam) and receives at least a portion of the at least one second imaging beam. In some embodiments, the at least one second imaging source may share the first detector with the first imaging source.

In some embodiments, the at least one second detector may be disposed in the first rotation portion. In some embodiments, the second rotation portion may include at least one opening corresponding to the at least one second detector. The at least one second detector may be configured to be set at a position corresponding to the at least one opening such that at least a portion of the at least one second imaging beam may pass through the at least one opening and impinge on the at least one second detector. For example, before the first rotation portion and the second rotation portion are locked, the first rotation portion and/or the second rotation portion may rotate to cause the at least one second detector to correspond to the at least one second opening. As another example, before the first rotation portion and the second rotation portion are locked, the at least one second detector may be movable to the position.

In some embodiments, a first component of the first rotation portion and a second component of the second rotation portion may be located on a first plane. The first component of the first rotation portion may include one or more of at least a portion of the treatment head, the third detector, the at least one second imaging source, the at least one second detector, etc. The second component of the second rotation portion may include one or more of the first imaging source, the first detector, the collimation component, the at least one second imaging source, the at least one second detector, etc. In some embodiments, the first component may include the first head portion. The second component may include the second head portion. In some embodiments, the first component may also include the first detector. In some embodiments, the second component may also include the first imaging source and the first detector.

In some embodiments, at least a portion (e.g., the first head portion, the second head portion, the whole treatment head) of the treatment head and at least one of the one or more imaging sources may be located on the first plane. In some embodiments, the one or more imaging sources may include the first imaging source (e.g., the CT imaging source). The at least a portion of the treatment head and the first imaging source may be located on the first plane. In some embodiments, the one or more imaging sources may include the first imaging source (e.g., a CT imaging source) and the at least one second imaging source (e.g., two DR imaging sources). The at least a portion of the treatment head and the first imaging source may be located on the same plane. The at least one second imaging source may be located on a plane different from the same plane. For example, the at least one second imaging source may be orientated obliquely with respect to the first plane. In some embodiments, the at least one second imaging source, the at least a portion of the treatment head, and/or at least one of the one or imaging sources may be located in the first plane. In some embodiments, the first detector and/or the third detector may also be located in the first plane.

In some embodiments, at least one of a third component of the first rotation portion and a fourth component of the second rotation portion may be disposed in at least one second plane. The at least one second plane may be different from the first plane. The third component of the first rotation portion may be different from the first component. The fourth component of the second rotation portion may be different from the second component. In some embodiments, the first plane and the at least one second plane may be planes (e.g., parallel planes) perpendicular to an axis of the gantry 111 (e.g., the z-axis). In some embodiments, there may be more than one second planes that are different from the first plane. The multiple second planes may be parallel to each other. For instance, the at least one second detector and the at least one second imaging source may be disposed in different second planes.

In some embodiments, the third component or the fourth component may include the microwave device, the acceleration device, the first cooing device, the high-voltage device, the at least one second imaging source, the at least one second detector, the second cooling device, or the like, or any combination thereof.

In some embodiments, the collimation component may be disposed in the first rotation portion. In some embodiments, the second rotation portion may include an opening. The collimation component may be configured to be set at a first position to correspond to the opening such that a portion of the treatment beam may be blocked by the collimation component and a portion of the treatment beam may pass through the collimation component towards the object via an opening of the collimation component. For example, the collimation component may be set at the first position by rotating the first rotation portion and/or the second rotation portion.

In some embodiments, one or more components of the first rotation portion may be moveable to a position (e.g., along a radial direction of the first rotation portion, along the negative z-axis in FIG. 1) such that the collimation component may correspond to the opening. For example, the one or more components of the first rotation portion may include the treatment source, the primary collimator, the filter, the chamber, the jaw, the secondary collimator, or the like, or any combination thereof. In some embodiments, at least one (e.g., the secondary collimator) of the one or more components of the first rotation portion may be moved into the opening. Merely by way of example, the whole treatment head may be moved into the opening such that a distance between the treatment source and the isocenter of the treatment head may be reduced. As another example, the primary collimator, the filter, the chamber, the jaw, and the secondary collimator may be moved into the opening. As a further example, the jaw and the secondary collimator may be moved into the opening.

In some embodiments, the one or more components may be mounted on a support component. The support component may be slidable along a guide rail via a drive mechanism. The one or more components may be moved by sliding the support component along the guide rail, for example, along a radial direction of the gantry 111.

In some embodiments, the second rotation portion and/or the first rotation portion may rotate to cause the treatment head to correspond to the opening. At least a portion of the first rotation portion may be moved downward (e.g., along a radial direction of the first rotation portion, the negative z-direction in FIG. 1) and into the opening. Further, the first rotation portion and the second rotation portion may be locked. The treatment head may be caused to emit the treatment beam to treat the region of the object. In some embodiments, during the radiation treatment, at least one of the one or more imaging sources may be caused to emit at least one imaging beam to the region of the object to perform an imaging of the region. Information acquired in the imaging process may be used to monitor or guide the radiation treatment. More descriptions of monitoring the radiation treatment process may be found elsewhere in the present disclosure. See, e.g., FIGS. 17 and 18, or the descriptions thereof.

In some embodiments, the collimation component may be disposed in the second rotation portion. The second rotation portion may include an opening. The first rotation portion and/or the second rotation portion may be configured to be set at a position such that at least a portion of the treatment beam may reach the collimation component via the opening. In some embodiments, the collimation component and the first imaging source may be arranged in parallel along a direction (e.g., a rotation axis of the second rotation portion, the x-direction, the y-direction, the z-direction in FIG. 1). In some embodiments, the collimation component and the imaging source may be movable, for example, along the direction. In some embodiments, the collimation component and the first imaging source may be arranged along a circumference of the second rotation portion.

In some embodiments, the imaging source and/or the collimation component may be movable to a first position such that the first imaging source may correspond to a region (e.g., the region) of an object to be imaged (e.g., the object) during an imaging of the object (also referred to as an acquisition mode). "Correspond to" used herein may refer that at least a portion of an imaging beam emitted by the first imaging source may pass through the region or a center of the imaging beam (e.g., the isocenter of the first imaging source) may correspond to a center of the region. In some embodiments, the first imaging source may also correspond to the first detector; that is, at least a portion of the imaging beam passing through the object may impinge on the detector.

In some embodiments, the collimation component and/or the imaging source may be movable to a second position such that the collimation component may correspond to a region (e.g., the region) of an object to be treated (e.g., the object) during a radiation treatment of the object (also referred to as a treatment mode). "Correspond to" used herein may refer that at least a portion of the treatment beam emitted by the treatment head may impinge on the region of the object via the collimation component. In some embodiments, the collimation component may also correspond to the third detector; that is, at least a portion of the treatment beam passing through the object may be received by the third detector.

In some embodiments, the collimation component may be connected to the first rotation portion. For example, the collimation component may be directly connected to a casing of the first rotation portion or connected to the casing via a bracket. As another example, the collimation component may be located inside the first rotation portion. The collimation component may be moved into the second rotation portion via an opening of the second rotation portion, e.g., during a treatment of the object. In some embodiments, the collimation component may be moved out of the second rotation portion, e.g., moved into a space of the first rotation portion during an imaging of the object.

In some embodiments, the collimation component may be movable to a first position of the first rotation portion during an imaging of the object. In some embodiments, the collimation component may be movable to a second position of the second rotation portion such that a position of the treatment beam corresponds to the collimation component during a radiation treatment of the object. In some embodiments, the collimation component may be movable along a direction (e.g., the x-axis, y-axis, and z-axis in FIG. 1). Before a radiation treatment of the object, the collimation component may be moved to the first position such that at least one of the one or more imaging sources in the second rotation portion (e.g., the first imaging source) rotates independently from the collimation component. Thus a rotation load of the second rotation portion (or the at least one imaging source) may be reduced, and the at least one imaging source may be rotated at a relatively high speed.

In some embodiments, before the treatment head is caused to emit a treatment beam to perform the radiation treatment, the collimation component may be moved to the second position corresponding to the first head portion such that at least a portion of the treatment beam may pass through the region of the object via the collimation component. In order to avoid a collision between the collimation component and the at least one imaging source and/or a collision between the collimation component and at least one of the at least one detector (e.g., the first detector), the first position may be set different from the second position.

In some embodiments, the collimation component may be disposed in an opening or an unoccupied space of the second rotation portion. The collimation component may be movable to a position (e.g., along the y-axis direction) outside the opening or the unoccupied space of the second rotation portion and fixed on the first rotation portion during an imaging of the object such that the imaging may be performed without the influence of the collimation component (e.g., a weight, a rotation speed), thereby improving the imaging speed and/or the imaging quality. In some embodiments, the collimation component may be movable to a position inside the opening or the unoccupied space such that a position of the treatment beam may correspond to a position of the collimation component.

In some embodiments, if the first head portion in the first rotation portion is unable to correspond to the collimation component by moving the collimation component, the second rotation portion may further rotate to a position such that the first head portion may correspond to the collimation component. It should be noted that the above descriptions may be for illustration purposes and non-limiting. In some embodiments, the second rotation portion may first rotate, and then the collimation component may be moved out of the opening or the unoccupied space of the second rotation portion such that the first head portion may correspond to the collimation component.

In some embodiments, the collimation component may be moved into an opening or an unoccupied space of the first rotation portion (e.g., along the x-axis direction in FIG. 1), and then the first imaging source may emit an imaging beam toward the object to perform an imaging of the object. In some embodiments, the collimation component may be moved out of the opening or the unoccupied space until the collimation component moves to a position such that the first head portion in the first rotation portion may correspond to the collimation component. Then the first head portion may emit a treatment beam towards the object to perform a treatment of the object.

By moving the collimation component and/or the first imaging source, the region of the object may be imaged during a radiotherapy at a position where the object is treated, thereby obviating the need to move the object between different treatment and imaging positions and obviating the need to perform position adjustments with respect to a treatment plan of the object, which in turn may save time and improve the utilization efficacy of the radiation system, alleviate the problems of different table sagging of the patient support between different treatment and imaging positions and resultant errors in a treatment performed at a treatment position based on imaging performed at an imaging position, and allow in-treatment imaging to facilitate in-treatment monitoring or tracking of the object, or a portion thereof, and a timely adjustment of the treatment execution accordingly.

In some embodiments, the at least one second imaging source may be disposed in the first rotation portion. The second rotation portion may include at least one opening. The at least one second imaging source may be configured to be set at a position such that at least a portion of the at least one second imaging beam may pass through the at least one opening, e.g., towards the region, that is, the at least one second imaging source may correspond to the at least one opening. For example, before the first rotation portion and the second rotation portion are locked, the first rotation portion and/or the second rotation portion may rotate such that the at least one second imaging source may correspond to the at least one opening. By arranging the at least one second imaging source in the first rotation portion, a load of the second rotation portion may be reduced, at least one of the one or more imaging sources disposed in the second rotation portion (e.g., the first imaging source) may rotate at a relatively high speed (e.g., smaller than 0.3 seconds per revolution, smaller than 0.5 seconds per revolution), thereby increasing an imaging speed, reducing imaging artifacts and/or improving an imaging quality.

In some embodiments, the at least one second imaging source may include two DR imaging sources. The second rotation portion may include two openings corresponding to the two DR imaging sources. Imaging beams emitted by the two DR imaging sources may pass through the two openings to the region of the object. In some embodiments, the at least one second imaging source may be fixed at a fixed position (e.g., on the stationary portion, on a wall, on the floor) of a room housing at least a portion of the radiation system 100 (e.g., the medical device 110), that is, the at least one second imaging source is not rotatable with the first imaging source. In some embodiments, the at least one second imaging source may be disposed in the second rotation portion.

In some embodiments, the at least one second imaging source may include at least two second imaging sources (e.g., DR imaging sources). An angle between axes of two imaging beams emitted by two of the at least two second imaging sources may be within an angular range, for example, a range between 70 degrees and 110 degrees, a range between 80 degrees and 100 degrees, a range between 85 degrees and 95 degrees, a range between 40 degrees and 120 degrees, a range between 30 degrees and 130 degrees, etc. Merely byway of example, the at least one second imaging source may include two second imaging sources (e.g., two DR imaging sources). An angle between axes of two imaging beams emitted by the two second imaging sources may be (substantially) 90 degrees e.g., 90°±10°. It should be noted that a count of the at least one second imaging source may be non-limiting, for example, one, two, three, four, five, etc.

In some embodiments, the medical device 110 may include a power supply configured to supply power to the at least one second imaging source and/or the at least one second detector. In some embodiments, the power supply may be disposed in the first rotation portion. In some embodiments, the power supply may be disposed in the second rotation portion. In some embodiments, the power supply, at least one of the at least one second imaging source, and at least one of the at least one second detector may be disposed in a same rotation portion (e.g., the first rotation portion, the second rotation portion).

In some embodiments, a non-coplanar radiation treatment may be performed on the object by tilting at least a portion of the gantry 111 or moving (e.g., rotating, translating) the patient support 113. During the non-coplanar radiation treatment, treatment beams emitted by the treatment head at different time points may be in different geometric planes.

In some embodiments, a multi-dimensional (e.g., two-dimensional, three-dimensional) non-coplanar radiation treatment may be achieved by tilting the gantry 111 and moving the patient support 113 together. By performing the non-coplanar radiation treatment or the multi-dimensional non-coplanar radiation treatment, an irradiation dose of normal tissue of the object may be effectively reduced while a radiation dose of the region is guaranteed, thereby improving the efficiency of the radiation treatment.

In some embodiments, the medical device 110 may include a tilting component. The tilting component may be configured to tilt at least a portion of the gantry 111 (e.g., the first rotation portion, the second rotation portion, the stationary portion) relative to a plane (e.g., the xz plane). For example, the at least a portion of the gantry 111 may be tilted relative to the plane by an angle, e.g., 5 degrees, 10 degrees, 20 degrees, 30 degrees, 40 degrees, 50 degrees, etc.

In some embodiments, the tilting component may include a frame configured to facilitate the tilting of at least a portion of the gantry 111 (e.g., one of the first rotation portion, the second rotation portion, or the stationary portion). In some embodiments, the at least a portion of the gantry 111 may be tilted by moving the frame such that the non-coplanar radiation treatment may be achieved. For example, the stationary portion, the first rotation portion, and the second rotation portion may be tilted by moving the frame.

In some embodiments, the tilting component may include a second frame. The second frame may be fixed on a floor of a room housing at least a portion of the radiation system 100 (e.g., the medical device 110 thereof). The second frame may be connected to the gantry 111 (e.g., the stationary portion thereof) and configured to fix the gantry 111. For example, the second frame may be fixed on the stationary portion via a bearing. In some embodiments, a first end of the frame may be connected to the second frame. A second end of the frame may be connected to the gantry 111 (e.g., the stationary portion thereof).

As described above, the patient support 113 may have the multiple (e.g., 6) degrees of freedom. In some embodiments, the non-coplanar radiation treatment may be achieved by rotating the patient support 113 an angle about a first axis (e.g., the z-axis n FIG. 1) of the gantry 111. In some embodiments, the non-coplanar radiation treatment may be achieved by translating the patient support 113 for a distance along a second axis (e.g., the x-axis, the y-axis in FIG. 1) of the gantry 111.

In some embodiments, after the gantry 111 is tilted and/or the patient support 113 is moved, the region of the object to be treated may deviate from the isocenter of the treatment head, which may affect the treatment efficacy and/or cause normal tissue of the object to receive unnecessary radiation. In order to solve the problems, the object may be further moved by moving the patient support 113 such that the center of the region may (substantially) coincide with the isocenter of the treatment head. That is, a deviation between the center of the region and the isocenter of the treatment head may be smaller than or equal to a threshold (e.g., a clinically allowable threshold (e.g., 5 millimeters)). For example, after the patient support 113 rotates about the first axis, the object may be moved by a certain distance along the x-direction and/or the y-direction such that the center of the region may coincide with the isocenter of the treatment head.

In some embodiments, each of the one or more imaging beams may cover an imaging region. The treatment beam may cover a treatment region. The one or more imaging sources and the treatment head may be configured such that the treatment region and the one or more imaging regions may at least partially overlap. In some embodiments, a region (e.g., a region to be treated) of the object may be placed in an overlapping region of the treatment region and the one or more imaging regions.

In some embodiments, the imaging assembly of the medical device 110 may be configured to perform a multi-energy imaging of the object. In some embodiments, the one or more imaging sources may include at least two imaging sources. The at least two imaging sources may be configured to emit at least two imaging beams of different energy levels. In some embodiments, one of the one or more imaging sources of the imaging assembly may emit different imaging beams of different energy levels. For example, the imaging source may emit the different imaging beams of different energy levels by adjusting a voltage of the imaging source. In some embodiments, one of the one or more imaging sources of the imaging assembly may emit a broad-spectrum imaging beam. At least one (e.g., a layer detector) of the at least one detector of the imaging assembly may divide an imaging beam (e.g., a portion of the broad-spectrum imaging beam that is detected) into different portions of different energy levels, each portion of which is of a same energy level.

As described above, the second rotation portion may be configured to rotate independently from the first rotation portion (e.g., in an unlocked state). In some embodiments, the second rotation portion and the first rotation portion may be controlled to rotate synchronously (e.g., in a locked state). In some embodiments, the medical device 110 may include a locking component. The locking component may be configured to lock the first rotation portion and the second rotation portion such that the first rotation portion and the second rotation portion rotate synchronously. In some embodiments, the medical device 110 may include at least one control component. The at least one control component may be configured to cause the first rotation portion and the second rotation portion to rotate synchronously. In some embodiments, the at least one control component may generate a control signal for controlling the first rotation portion and the second rotation portion to rotate at a same speed and in a same direction.

In some embodiments, there may be at least one control component, e.g., one, two, or more. For example, the medical device 110 may include one control component. The control component may transmit the control signal to the first rotation component and the second rotation component, respectively. As another example, the medical device 110 may include two control components. One of the two control components may generate a control signal and transmit thereof to the first rotation portion. A remaining one of the two control components may generate another control signal and transmit thereof to the second rotation portion. In some embodiments, an operator (e.g., an imaging technician) of the radiation system 100 may cause the at least one control component to generate the control signal(s).

In some embodiments, before the treatment head is caused to emit a treatment beam towards a region (e.g., a region to be treated) of the object to perform a radiation treatment of the object, the first rotation portion and the second rotation portion may be controlled in the unlocked state. The second rotation portion may rotate independently from the first rotation portion to perform an imaging of the region of the object. In such cases, the second rotation portion may rotate without the influence of the first rotation portion, and rotate at a relatively high speed (e.g., smaller than 0.3 seconds per revolution, smaller than 0.5 seconds per revolution), thereby completing the imaging within a short time, reducing imaging artifacts and/or improving an imaging quality.

In some embodiments, information (e.g., an imaging dataset, an image (e.g., a 3D image)) acquired in the imaging process may be used to guide a positioning of the region and/or adjust a treatment plan of the region. More descriptions of guiding the positioning of the region and/or adjusting the treatment plan may be found elsewhere in the present disclosure. See, e.g., FIG. 17, 18, or the descriptions thereof.

In some embodiments, after the region of the object is positioned in the radiation system 100 based on the information acquired in the imaging process or after the imaging of the object is completed, the first rotation portion and the second rotation portion may be locked via the locking component and/or the at least one control component, that is in the locked state. The treatment head may then be caused to emit the treatment beam to treat the region of the object. In some embodiments, during the radiation treatment, at least one (e.g., the CT imaging source, the at least one DR imaging source) of the one or more imaging sources may be caused to emit another at least one imaging beam to the region of the object to perform another imaging of the region. In some embodiments, information acquired in the imaging process may be used to monitor the radiation treatment. More descriptions of monitoring the radiation treatment may be found elsewhere in the present disclosure. See, e.g., FIG. 17, 18, or the descriptions thereof.

According to some embodiments of the present disclosure, a radiation system may be provided. The radiation system may include a first rotation portion and a second rotation portion. The second rotation portion may be able to rotate independently from the first rotation portion. In some embodiments, the first rotation portion may include a first component assembly and a first rotor configured to facilitate a rotation of at least one of the first component assembly. The second rotation portion may include a second component assembly and a second rotor configured to facilitate a rotation of at least one of the second component assembly. It should be noted that the above descriptions may be non-limiting. In some embodiments, the first rotation portion may be considered as the first rotor, and the first component assembly may be disposed in the first rotor or the first rotation portion. The second rotation portion may be considered as the second rotor, and the second component assembly may be disposed in the second rotor or the second rotation portion. More descriptions of the radiation system may be found elsewhere in the present disclosure, for example, FIGS. 1-13 or the descriptions thereof.

According to some embodiments of the present disclosure, a radiation system may be provided. The radiation system may include a first rotation portion, a second rotation portion, a treatment head, one or more imaging sources, and at least one detector. The treatment head may include a first portion (also referred to as a first head portion) configured to emit a treatment beam towards an object and a second portion (also referred to as a second head portion) configured to adjust a radiation range of the treatment beam. In some embodiments, the second head portion may be movable with respect to the first head portion. The first head portion may be disposed in the first rotation portion. In some embodiments, at least one of the one or more imaging sources may be disposed in the second rotation portion. In some embodiments, the second head portion may be able to move as an integral piece with respect to the first head portion in the form of, for example, translation along or rotation about a direction (e.g., a rotation axis of the second rotation portion, the x-direction, the y-direction, the z-direction in FIG. 1). For example, the second head portion and the second rotation portion may move together with respect to the first head portion.

In some embodiments, the second rotation portion may include a space for accommodating the second portion of the treatment head.

In some embodiments, the second portion of the treatment head may be moveable into the space of the second rotation portion.

In some embodiments, the second rotation portion may be configured to rotate, at a first speed, independently from the first rotation portion during an imaging of the object.

In some embodiments, the second rotation portion and the first rotation portion may be configured to rotate synchronously at a second speed during a treatment of the object.

In some embodiments, the first speed may be higher than the second speed.

In some embodiments, the second portion of the treatment head may be disposed in the second rotation portion. The second portion of the treatment head and at least one of the one or more imaging sources may be arranged along a circumferential direction of the second rotation portion.

In some embodiments, the second portion of the treatment head and at least one of the one or more imaging sources may be arranged along a rotation axis of the second rotation portion. The second portion of the treatment head and the at least one of the one or more imaging sources may be configured to move along the rotation axis. In some embodiments, the at least one of the one or more imaging sources may rotate independently from the collimation component. In some embodiments, the at least one of the one or more imaging sources and the collimation component may rotate synchronously.

In some embodiments, the second portion of the treatment head may be movable between the first rotation portion and the second portion and connected to the first rotation portion.

In some embodiments, the second portion of the treatment head may be disposed in the first rotation portion during an imaging of the object, such that a load of the second rotation portion may be reduced, and at least one of the one or more imaging sources disposed in the second rotation portion may rotate at a relatively high speed, thereby increasing an imaging speed, reducing imaging artifacts and/or improving an imaging quality. In some embodiments, the second portion of the treatment head may be moved into the second rotation portion during a treatment of the object.

In some embodiments, the second rotation portion may rotate independently from the second portion of the treatment head during an imaging of the object.

In some embodiments, each of the first rotation portion and the second rotation portion may be connected to a stationary portion via a bearing.

In some embodiments, the first rotation portion may be connected to a stationary portion via a first bearing, and the second rotation portion may be connected to the first rotation portion via a second bearing.

In some embodiments, the radiation system may include a tilting component configured to facilitate a tilting of at least one of the first rotation portion, the second rotation portion, or the stationary portion.

In some embodiments, the tilting component may include a frame configured to tilt the stationary portion so as to facilitate the tilting of the at least one of the first rotation portion, the second rotation portion, or the stationary portion.

In some embodiments, the first rotation portion may include an electronic portal imaging device (EPID) configured to detect at least a portion of the treatment beam.

In some embodiments, the one or more imaging sources may include a computed tomography (CT) imaging source or at least one digital radiography (DR) imaging source. In some embodiments, the at least one detector may include a first detector corresponding to the CT imaging source or at least one second detector corresponding to the at least one DR imaging source.

In some embodiments, the at least one DR imaging source or the at least one second detector may be fixed at a fixed position of a room housing at least a portion of the radiation system.

In some embodiments, the at least one DR imaging source and at least one second detector may be disposed in at least one of the first rotation portion or the second rotation portion.

In some embodiments, at least one component of the first rotation portion and at least one component of the second rotation portion may be located on a same plane.

In some embodiments, the first rotation portion may be outside the second rotation portion.

In some embodiments, the radiation system may include a locking component configured to lock the first rotation portion and the second rotation portion such that the first rotation portion and the second rotation portion rotate synchronously during a treatment of the object.

The network 150 may facilitate exchange of information and/or data. In some embodiments, one or more components of the radiation system 100 (e.g., the medical device 110, the processing device 120, the storage device 130, or the terminal 140) may send information and/or data to another component(s) in the radiation system 100 via the network 150. For example, the processing device 120 may obtain a user instruction from the terminal 140 via the network 150. As another example, the processing device 120 may obtain scan data (e.g., projection data) from the medical device 110 via the network 150. In some embodiments, the network 150 may be any type of wired or wireless network, or combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired or wireless network access points such as base stations and/or internet exchange points through which one or more components of the radiation system 100 may be connected to the network 150 to exchange data and/or information.

The terminal 140 may include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 140 may remotely operate the medical device 110. In some embodiments, the terminal 140 may operate the medical device 110 via a wireless connection. In some embodiments, the terminal 140 may receive information and/or instructions inputted by a user, and send the received information and/or instructions to the medical device 110 or to the processing device 120 via the network 150. In some embodiments, the terminal 140 may receive data and/or information from the processing device 120. In some embodiments, the terminal 140 may be part of the processing device 120. In some embodiments, the terminal 140 may be omitted.

In some embodiments, the processing device 120 may process data obtained from the medical device 110, the storage device 130, or the terminal 140. For example, the processing device 120 may obtain projection data of an object from the medical device 110 and generate an image of the object based on the projection data. As another example, the processing device 120 may cause one or more components (e.g., the treatment head, the one or more imaging sources, the first detector, the at least one second detector, the third detector, the collimation component, the patient support 113, the gantry 111, etc.) of the medical device 110 to be located at a specific position. The processing device 120 may be a central processing unit (CPU), a digital signal processor (DSP), a system on a chip (SoC), a microcontroller unit (MCU), or the like, or any combination thereof.

In some embodiments, the processing device 120 may be a single server or a server group. The server group may be centralized or distributed. In some embodiments, the processing device 120 may be local or remote. For example, the processing device 120 may access information and/or data stored in the medical device 110, the storage device 130, and/or the terminal 140 via the network 150. As another example, the processing device 120 may be directly connected to the medical device 110, the storage device 130, and/or the terminal 140, to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data and/or instructions. In some embodiments, the storage device 130 may store data obtained from the terminal 140 and/or the processing device 120. For example, the storage device 130 may store one or more images generated by the processing device 120. In some embodiments, the storage device 130 may store data and/or instructions that the processing device 120 may execute or use to perform exemplary methods described in the present disclosure. For example, the storage device 130 may store instructions that the processing device 120 may execute or use to generate one or more images based on projection data. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more components of the radiation system 100 (e.g., the medical device 110, the processing device 120, the terminal 140). One or more components of the radiation system 100 may access the data or instructions stored in the storage device 130 via the network 150. In some embodiments, the storage device 130 may be directly connected to or communicate with one or more components of the radiation system 100 (e.g., the processing device 120, the terminal 140). In some embodiments, the storage device 130 may be part of the processing device 120.

FIG. 2 is a section view illustrating an exemplary medical device according to some embodiments of the present disclosure.

As shown in FIG. 2, the medical device 200 may include a stationary portion 210, a first rotation portion 220, and a second rotation portion 230. The stationary portion 210 may be connected to the first rotation portion 220 and the second rotation portion 230, respectively. In some embodiments, the first rotation portion 220 may be configured to move (e.g., rotate) independently from the second rotation portion 230. The first rotation portion 220 may rotate about a first ring, and the second rotation portion 230 may rotate about a second ring different from the first ring. In some embodiments, a radius of the first ring may be larger than a radius of the second ring. In some embodiments, the first ring and the second ring may be coplanar. For example, the first ring and the second ring may be concentric shown in FIG. 2.

As shown in FIG. 2, the medical device 200 may include a first head portion 221, a detector 222 (e.g., an EPID), an imaging source 231 (e.g., a CT imaging source), a detector 232 (e.g., a curvilinear detector, a flat panel detector), and a second head portion 233 (also referred to as a collimation component 233). In some embodiments, the first head portion 221 may be configured to emit a treatment beam (e.g., a treatment beam 234 in FIGS. 4-7 or 11) toward a region (e.g., a region to be treated) (e.g., a region 282 in FIGS. 4-7, 9-11, 13, or 14) of an object (e.g., an object 280 in FIGS. 4-7, 9-11, 13, or 14). The detector 222 may be configured to receive at least a portion of the treatment beam. The collimation component 233 may be configured to adjust a radiation range of the treatment beam. The imaging source 231 may be configured to emit an imaging beam (e.g., an imaging beam 310 in FIG. 3) toward the region of the object. The detector 232 may be configured to detect at least a portion of the imaging beam. In some embodiments, a fan angle of the imaging beam emitted by the imaging source 231 may be adjusted, for example, by a collimator. The collimator may include at least one leaf. The fan angle of the imaging beam may be adjusted by moving at least one of the at least one leaf.

As shown in FIG. 2, the first head portion 221 and the detector 222 may be disposed in the first rotation portion 220. The imaging source 231, the detector 232, and the collimation component 233 may be disposed in the second rotation portion 230. In some embodiments, the first head portion 221, the detector 222, the imaging source 231, the detector 232, and the second head portion 233 may be located on a same plane (e.g., the xz plane).

In some embodiments, the imaging beam emitted by the imaging source 231 may cover an imaging region. The treatment beam emitted by the first head portion 221 may cover a treatment region. The imaging source 231 and the first head portion 221 may be configured such that the treatment region and the imaging region may at least partially overlap. In some embodiments, the region of the object may be placed in an overlapping region of the treatment region and the imaging region.

FIG. 3 is a section view illustrating an exemplary medical device according to some embodiments of the present disclosure. The medical device 300 may be the same as or similar to the medical device 200 in FIG. 2.

As shown in FIG. 3, similar to the medical device 200, the medical device 300 may include the first head portion 221, the detector 222 (e.g., the EPID), the imaging source 231 (e.g., the CT imaging source), the detector 232 (e.g., the curvilinear detector, the flat panel detector), and the collimation component 233. In some embodiments, the first rotation portion 220 may be configured to move (e.g., rotate) independently from the second rotation portion 230. For example, the second rotation portion 230 may rotate in a clockwise direction (e.g., a direction indicated by an arrow a in FIG. 3). As another example, the second rotation portion 230 may rotate in an anticlockwise direction (e.g., a direction opposite to the direction indicated by the arrow a in FIG. 3). More descriptions of the medical device 300 may be found elsewhere in the present disclosure. See, for example, FIG. 2 or the descriptions thereof.

In some embodiments, the first head portion 221 may be caused to emit a treatment beam (e.g., the treatment beam 234 in FIGS. 4-7 or 11) towards a region (e.g., the region 282 in FIGS. 4-7, 9-11, 13, or 14) (e.g., a region to be treated) of the object 280 to perform a radiation treatment of the region. In some embodiments, before the radiation treatment of the region, the imaging source 231 may be caused to emit the imaging beam 310 toward the object 280 in FIG. 3. In some embodiments, the imaging beam 310 may have a relatively large fan angle. For example, the fan angle of the imaging beam 310 may be a maximum fan angle of an imaging beam emitted by the imaging source 231.

In some embodiments, an imaging dataset may be generated based on at least a portion of the imaging beam 310 detected by the detector 232. An image (e.g., a 3D image) may be generated based on at least a portion of the imaging dataset. The image may be used to guide a positioning of the region of the object 280 or adjust a treatment plan of the object 280. More descriptions of guiding the positioning of the region and/or adjusting the treatment plan may be found elsewhere in the present disclosure. See, for example, FIGS. 17, 18, or the descriptions thereof.

FIG. 4 is a section view illustrating an exemplary medical device according to some embodiments of the present disclosure. The medical device 400 may be the same as or similar to the medical device 200 in FIG. 2 or the medical device 300 in FIG. 3.

As shown in FIG. 4, the medical device 400 may include the first head portion 221, the detector 222 (e.g., the EPID), the imaging source 231 (e.g., the CT imaging source), the detector 232 (e.g., the curvilinear detector, the flat panel detector), and the collimation component 233. The medical device 400 may also include a locking component 410. The locking component 410 may be configured to lock the first rotation portion 220 and the second rotation portion 230 such that the first rotation portion 220 and the second rotation portion 230 may rotate synchronously. More descriptions of the medical device 400 may be found elsewhere in the present disclosure. See, for example, FIGS. 2, 3, or the descriptions thereof.

In some embodiments, after a positioning of the region 282 of the object 280 is completed or after the imaging of the object is completed, the first rotation portion 220 and/or the second rotation portion 230 may rotate such that the collimation component 233 may correspond to the first head portion 221 in the first rotation portion 220. Then the first rotation portion 220 and the second rotation portion 230 may be locked. The first head portion 221 may be caused to emit the treatment beam 234 to perform a radiation treatment of the region 282 of the object 280. "Correspond" used herein may refer that a first portion of the treatment beam 234 may be blocked by the collimation component 233 and a second portion of the treatment beam 234 may pass through the collimation component 233 towards the region 282 via an opening of the collimation component 233. In some embodiments, the collimation component 233 may include a multi-leaf collimator (MLC) and/or a jaw. A size and/or a shape of the opening of the collimation component 233 may be adjusted by moving at least a portion of a plurality of leaves of the MLC and/or the jaw. In some embodiments, the collimation component 233 may be set to correspond to the first head portion 221 in the first rotation portion 220, and the first rotation portion 220 and the second rotation portion 230 may be locked directly without the rotation operation described above.

FIG. 5 is a section view illustrating an exemplary medical device according to some embodiments of the present disclosure.

As shown in FIG. 5, the medical device 500 may include a treatment head 570, the detector 222 (e.g., the EPID), the locking component 410, an imaging source 510 (e.g., a DR imaging source), an imaging source 520 (e.g., a DR imaging source), a detector 530 (e.g., a flat panel detector), and a detector 540 (e.g., a flat panel detector). In some embodiments, the treatment head 570 may include a first head portion (e.g., the first head portion in FIG. 1 or the first head portion 221 in FIGS. 2-4) and a second head portion (e.g., the second head portion in FIG. 1 or the second head portion 233 in FIGS. 2-4). The imaging source 510 may be configured to emit an imaging beam 560 toward the region 282 of the object 280. The detector 540 may be configured to receive at least a portion of the imaging beam 560. The imaging source 520 may be configured to emit an imaging beam 550 toward the region 282 of the object 280. The detector 530 may be configured to receive at least a portion of the imaging beam 550. In some embodiments, the medical device 500 may also include the first imaging source (not shown in FIG. 5) and the first detector (not shown in FIG. 5) described elsewhere in the present disclosure, for example, the first imaging source and the first detector in FIG. 1, the imaging source 231 and the detector 232 in FIGS. 2-4, etc.

As shown in FIG. 5, the treatment head 570 and the detector 222 may be disposed in the first rotation portion 220. The detectors 530 and 540 may be disposed in the stationary portion 210. The imaging sources 510 and 520 may be disposed on a floor of a room housing the medical device 500.

In some embodiments, the first rotation portion 220 and the second rotation portion 230 may be locked and rotate in a direction as indicated by an arrow p in FIG. 5. The treatment head 570 may be caused to emit the treatment beam 234 to perform a radiation treatment of the object 280. In some embodiments, during the radiation treatment of the object 280, the imaging sources 510 and 520 may be caused to emit the imaging beams 560 and 550. An imaging dataset may be generated based on at least a portion of the imaging beam 550 and at least a portion of the imaging beam 560 detected by the detectors 530 and 540, respectively. In some embodiments, images may be generated based on the imaging datasets, respectively. The images may be used to monitor the radiation treatment of the object 280, for example, determine whether to adjust a position of the region 282, adjust a delivery of the treatment beam 234, and/or adjust a treatment plan of the region 282. More descriptions of monitoring the radiation treatment may be found elsewhere in the present disclosure. See, for example, FIGS. 17, 18, or the descriptions thereof.

In some embodiments, the imaging beams 550 and 560 emitted by the imaging sources 520 and 510 may cover an imaging region, respectively. The treatment beam 234 emitted by the treatment head 570 may cover a treatment region. The imaging sources 510 and 550 and the treatment head 570 may be configured such that the treatment region and the imaging regions at least partially overlap. In some embodiments, the region 282 of the object 280 (e.g., a region to be treated) may be placed in an overlapping region of the treatment region and the imaging regions.

As described above, the treatment head 570 may be disposed in the first rotation portion 220 in FIG. 5. It should be noted that the above descriptions may be for illustration purposes and non-limiting. In some embodiments, the first head portion of the treatment head 570 may be disposed in the first rotation portion 220 in FIG. 5. The second head portion of the treatment head 570 may be disposed in the second rotation portion.

FIG. 6 is a section view illustrating an exemplary medical device according to some embodiments of the present disclosure.

As shown in FIG. 6, the medical device 600 may include the first head portion 221, the detector 222 (e.g., the EPID), the imaging source 231 (e.g., the CT imaging source), the detector 232 (e.g., the curvilinear detector, the flat panel detector), the imaging source 510 (e.g., the DR imaging source), the imaging source 520 (e.g., the DR imaging source), the detector 530 (e.g., the flat panel detector), and the detector 540 (e.g., the flat panel detector). The first head portion 221 and the detector 222 may be disposed in the first rotation portion 220. The collimation component 233, the imaging source 510, the imaging source 231, the imaging source 520, the detector 540, the detector 530, and the detector 232 may be disposed in the second rotation portion 230.

In some embodiments, the first head portion 221 may be caused to emit the treatment beam 234 to perform a radiation treatment of the region 282 of the object 280. In some embodiments, during the radiation treatment of the region 282 of the object 280, the imaging sources 510 and 520 may be caused to emit the imaging beams 560 and 550, respectively in FIG. 6. An imaging dataset may be generated based on at least a portion of the imaging beam 550 and at least a portion of the imaging beam 560 detected by the detectors 530 and 540, respectively. In some embodiments, images may be generated based on the imaging datasets, respectively. The images may be used to monitor the radiation treatment of the object 280, for example, determine whether to adjust a position of the region 282, adjust a delivery of the treatment beam 234, and/or adjust a treatment plan of the region 282. More descriptions of monitoring the radiation treatment may be found elsewhere in the present disclosure. See, for example, FIGS. 17, 18, or the descriptions thereof. As shown in FIG. 6, an angle between an axis of the imaging beam 550 and an axis of the imaging beam 560 may be (substantially) 90 degrees.

It should be noted that the above descriptions are for illustration purposes and non-limiting. During the radiation treatment of the region 282 of the object 280, the imaging source 231 may be also caused to emit an imaging beam towards the region 282 to perform an imaging of the object, a fan angle of which may be smaller than a fan angle of the imaging beam 310. In some embodiments, before the radiation treatment of the region 282 of the object, the imaging source 231 may be caused to emit the imaging beam 310 of a relatively large fan angle to perform an imaging of the object. The imaging result may be used to guide a positioning of the region 282 and/or adjust a treatment plan of the object 280. In some embodiments, the detectors 530 and 540 may be movable to a position to prevent the detectors 530 and 540 from blocking a pathway of at least a portion of the imaging beam emitted of the relatively large fan angle. For example, the detectors 530 and 540 may be moved outside a range of the imaging beam emitted of the relatively large fan angle.

In some embodiments, the imaging beams emitted by the imaging sources 231, 510, and 520 may cover an imaging region, respectively. The treatment beam emitted by the first head portion 221 may cover a treatment region. The imaging sources 231, 510, and 550 and the first head portion 221 may be configured such that the treatment region and the imaging regions at least partially overlap. In some embodiments, the region 282 of the object 280 (e.g., a region to be treated) may be placed in an overlapping region of the treatment region and the imaging regions.

FIG. 7 is a section view illustrating an exemplary medical device according to some embodiments of the present disclosure.

As shown in FIG. 7, similar to the medical device 600 in FIG. 6, the medical device 700 may include the first head portion 221, the detector 222 (e.g., the EPID), the imaging source 231 (e.g., the CT imaging source), the detector 232 (e.g., the curvilinear detector, a flat panel detector), the imaging source 510 (e.g., the DR imaging source), the imaging source 520 (e.g., the DR imaging source), the detector 530 (e.g., the flat panel detector), and the detector 540 (e.g., the flat panel detector). More descriptions of the medical device 700 may be found elsewhere in the present disclosure. See, for example, FIG. 6 or the descriptions thereof.

As shown in FIG. 7, the first head portion 221, the imaging source 510, and the imaging source 520 may be disposed in the first rotation portion 220. The imaging source 231, the detector 222, the detector 540, the detector 530, the detector 232, and the collimation component 233 may be disposed in the second rotation portion 230. In some embodiments, the first head portion 221, the detector 222, the imaging source 231, the detector 232, the imaging source 510, the imaging source 520, the detector 530, and the detector 540 may be located on a same plane (e.g., the xz plane).

In some embodiments, the second rotation portion 230 may include an opening. The first rotation portion 220 and/or the second rotation portion 230 may be configured to be set at a position such that at least a portion of the treatment beam 234 may reach the collimation component 233 via the opening.

In some embodiments, the imaging beams emitted by the imaging source 231, the imaging source 510, and/or the imaging source 520 may cover an imaging region, respectively. The treatment beam 234 emitted by the first head portion 221 may cover a treatment region. The imaging sources 231, 510, and/or 520 and the first head portion 221 may be configured such that the treatment region and the imaging regions may at least partially overlap. In some embodiments, the region 282 of the object 280 may be placed in an overlapping region of the treatment region and the imaging regions.

Figure 8:
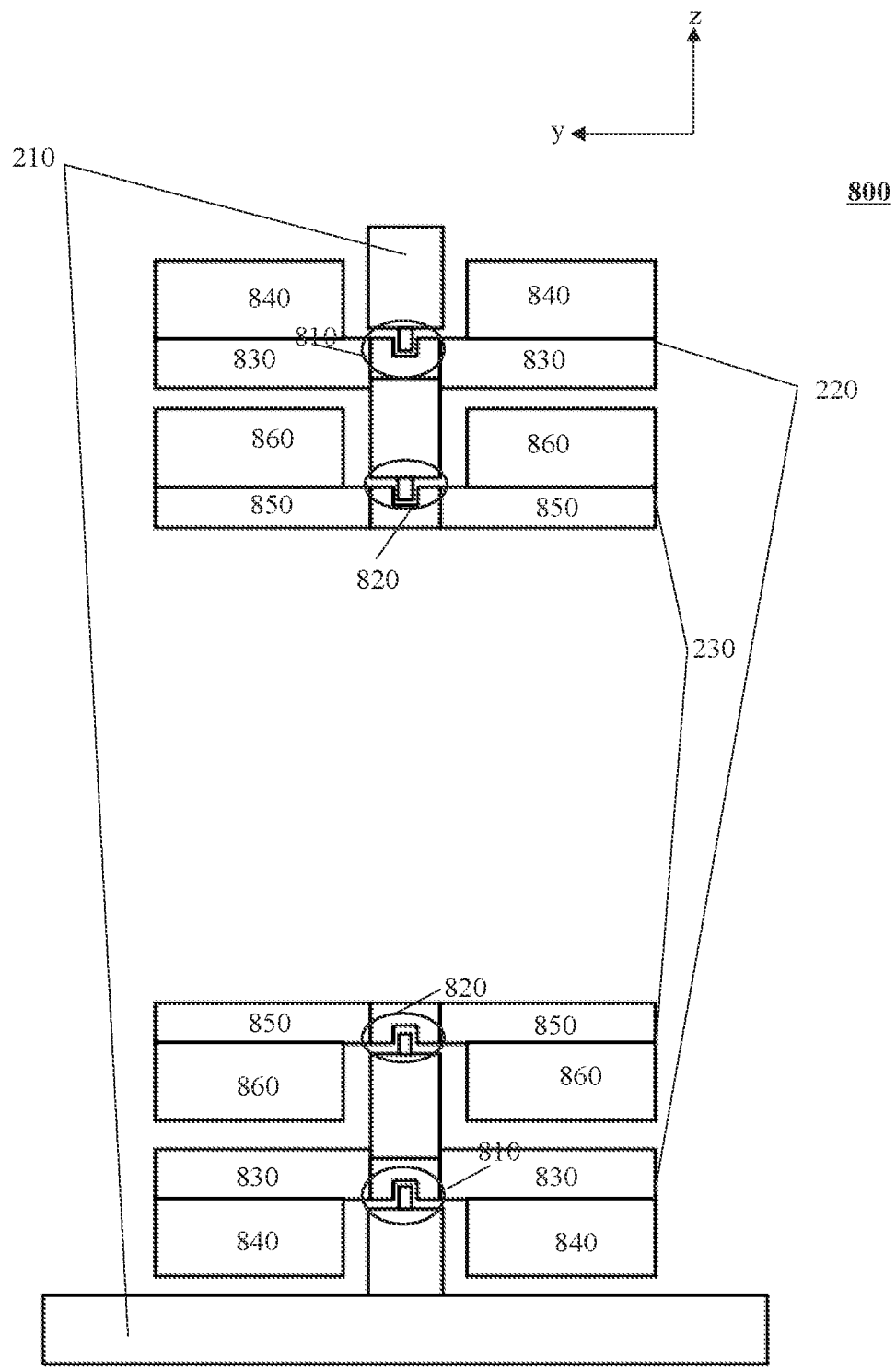
FIG. 8 is a section view illustrating an exemplary medical device according to some embodiments of the present disclosure.

FIG. 8 is a section view illustrating an exemplary medical device according to some embodiments of the present disclosure.

As shown in FIG. 8, the medical device 800 may include the stationary portion 210, the first rotation portion 220, and the second rotation portion 230. The first rotation portion 220 may be connected to the stationary portion 210 via a bearing 810. The second rotation portion 230 may be connected to the first rotation portion 220 via a bearing 820.

In some embodiments, the first rotation portion 220 may be configured to move (e.g., rotate) independently from the second rotation portion 230. The first rotation portion 220 may rotate about a first ring, and the second rotation portion 230 may rotate about a second ring different from the first ring. In some embodiments, a radius of the first ring may be larger than a radius of the second ring. In some embodiments, the first ring and the second ring may be coplanar. For example, the first ring and the second ring may be concentric.

In some embodiments, similar to the medical devices 400 and 500 in FIG. 4 and FIG., the medical device 800 may include a locking component (e.g., the locking component 410 in FIG. 4 and FIG. 5) or at least one control component (e.g., the at least one control component in FIG. 1) (not shown in FIG. 8). For example, the first rotation portion 220 and the second rotation portion 230 may rotate synchronously by locking the first rotation portion 220 and the second rotation portion 230 via the locking component or the at least one control component. As another example, the second rotation portion 230 may rotate independently from the first rotation portion 220 by unlocking the first rotation portion 220 and the second rotation portion 230 via the locking component or the at least one control component. More descriptions of the locking component 410 or the at least one control component may be found elsewhere in the present disclosure. See, for example, FIGS. 1, 4, or the descriptions thereof.

As shown in FIG. 8, the first rotation portion 220 may include a rotor 830 and a component assembly 840 connected to the rotor 830. The rotor 830 may be configured to cause the component assembly 840 to rotate. The second rotation portion 230 may include a rotor 850 and a component assembly 860 connected to the rotor 850. The rotor 850 may be configured to cause the component assembly 860 to rotate. In some embodiments, the component assembly 840 may be the same as or similar to the first component assembly in FIG. 1. The component assembly 860 may be the same as or similar to the second component assembly in FIG. 1. For example, the component assembly 840 may include the first head portion 221, the imaging source 510, and the imaging source 520. The component assembly 860 may include the collimation component 233, the imaging source 231, the detector 222, the detector 540, the detector 530, and the detector 232.

FIG. 9 and FIG. 10 are section views illustrating an exemplary medical device according to some embodiments of the present disclosure.

As shown in FIG. 9 and FIG. 10, the collimation component 233 and the imaging source 231 may be arranged in parallel along a direction indicated by an arrow a in FIG. 9. In some embodiments, the collimation component 233 and the imaging source 231 may be movable along the direction. In some embodiments, the imaging source 231 and/or the collimation component 233 may be movable to a first position such that the imaging source 231 may correspond to a region (e.g., the region 282) of an object (e.g., the object 280) to be imaged during an imaging of the object. "Correspond" used herein may refer that at least a portion of an imaging beam emitted by the imaging source 231 may pass through the region. For example, as shown in FIG. 9, the collimation component 233 and the imaging source 231 may be moved to the first position, and then the imaging source 231 may be caused to emit an imaging beam. In some embodiments, the imaging source 231 may also correspond to the detector 232; that is, at least a portion of the imaging beam passing through the object may be received by the detector 232.

In some embodiments, the collimation component 233 and/or the imaging source 231 may be movable to a second position such that the collimation component 233 may correspond to a region (e.g., the region 282) of an object (e.g., the object 280) to be treated during a radiation treatment of the object. For example, as shown in FIG. 10, the collimation component 233 and the imaging source 231 may be moved to the second position, and then a first head portion of the treatment head may be caused to emit the treatment beam. In some embodiments, the collimation component 233 may also correspond to the detector 222; that is, at least a portion of the treatment beam passing through the object may be received by the detector 222.

In some embodiments, the imaging source 231 may rotate independently from the collimation component 233. The imaging source 231 and the detector 232 may be fixed, via one or more first bearings, on a support component 870. The support component 870 may be configured to support both the collimation component 233 and the imaging source 231.

In some embodiments, the imaging source 231 and the collimation component 233 may rotate synchronously. The imaging source 231, the detector 232, and the collimation component 233 may be fixed on the support component 870 via one or more second bearings.

In some embodiments, the imaging beam emitted by the imaging source 231 may cover an imaging region. The treatment beam emitted by the first head portion may cover a treatment region. The imaging source 231 and the first head portion may be configured such that the treatment region and the imaging regions at least partially overlap. In some embodiments, the region 282 of the object 280 may be placed in an overlapping region of the treatment region and the imaging regions.

Figure 12:
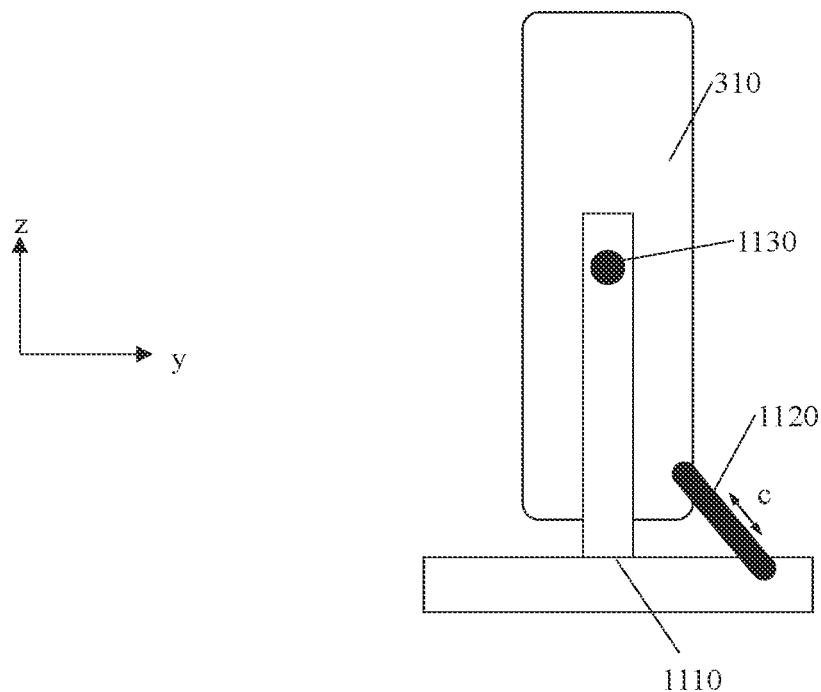

FIG. 11 and FIG. 12 are section views illustrating an exemplary medical device according to some embodiments of the present disclosure.

As shown in FIG. 11, similar to the medical device 700, the medical device 1100 may include the first head portion 221, the detector 222 (e.g., the EPID), the imaging source 231 (e.g., the CT imaging source), the detector 232 (e.g., the curvilinear detector, the flat panel detector), the imaging source 510 (e.g., the DR imaging source), the imaging source 520 (e.g., the DR imaging source), the detector 530 (e.g., the flat panel detector), and the detector 540 (e.g., the flat panel detector). The first head portion 221, the imaging source 510, and the imaging source 520 may be disposed in the first rotation portion 220. The imaging source 231, the detector 222, the detector 540, the detector 530, the detector 232, and the collimation component 233 may be disposed in the second rotation portion 230. The stationary portion 210 may be connected to the first rotation portion 220 and the second rotation portion 230.

As shown in FIG. 11 and FIG. 12, the medical device 1100 may include a frame 1110 and a frame 1120. The frame 1110 may be fixed on a floor of a room housing the medical device 1100. The frame 1110 may be connected to the stationary portion 210 at a point 1130. The frame 1110 may be configured to stabilize the stationary portion 210. The frame 1120 may be connected to the stationary portion 210 and the frame 1110. The stationary portion 210, the first rotation portion 220, and the second rotation portion 230 may be tilted by moving the frame 1110. In some embodiments, by moving the frame 1120 along a direction c in FIG. 12, the medical device 1100 (e.g., a gantry thereof) may tilt by an angle relative to a direction indicated by an arrow a in FIG. 11, thereby achieving a non-coplanar treatment of the object 280 during a radiation treatment of the region 282 of the object 280. It should be noted that the above descriptions are non-limiting. For example, the frame 1120 may move along the x-axis, the z-axis, the y-axis in FIG. 11.

Figure 13:
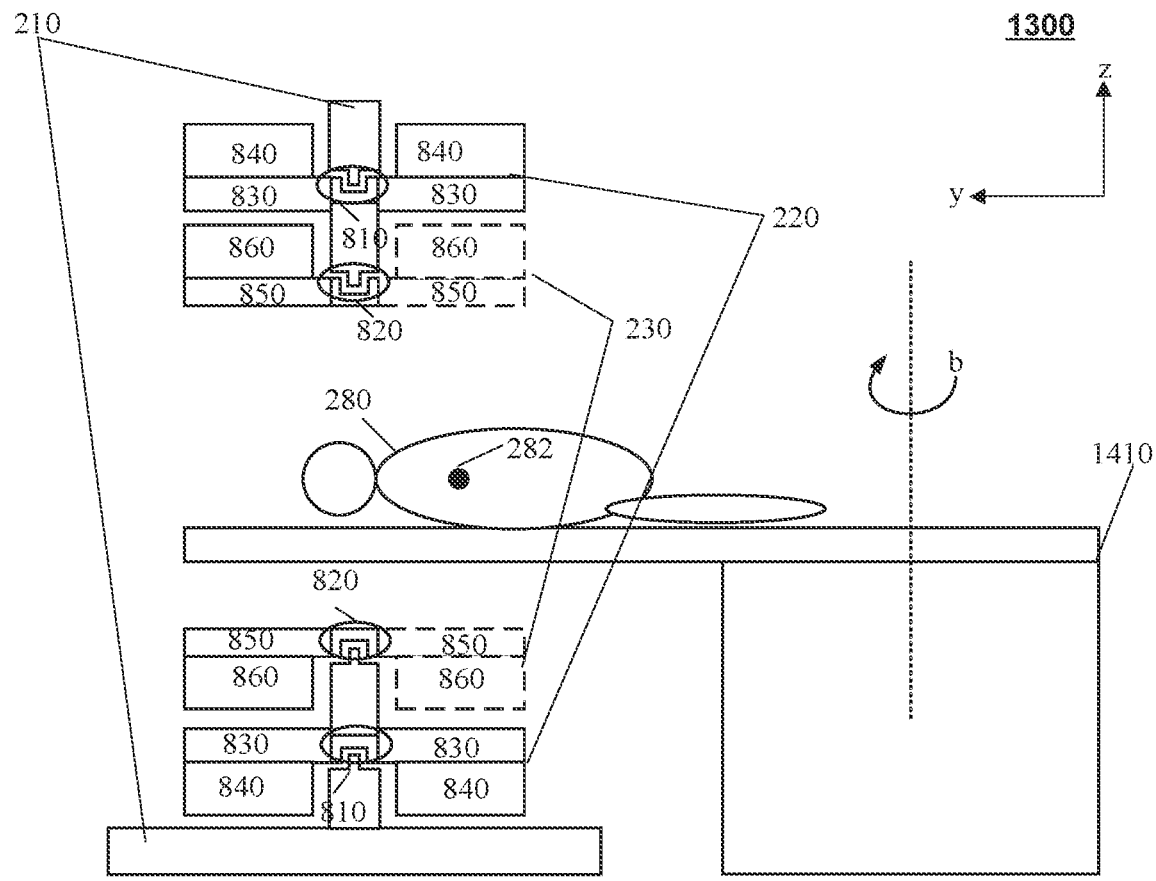
FIG. 13 and FIG. 14 are section views illustrating an exemplary medical device according to some embodiments of the present disclosure.
Figure 14:
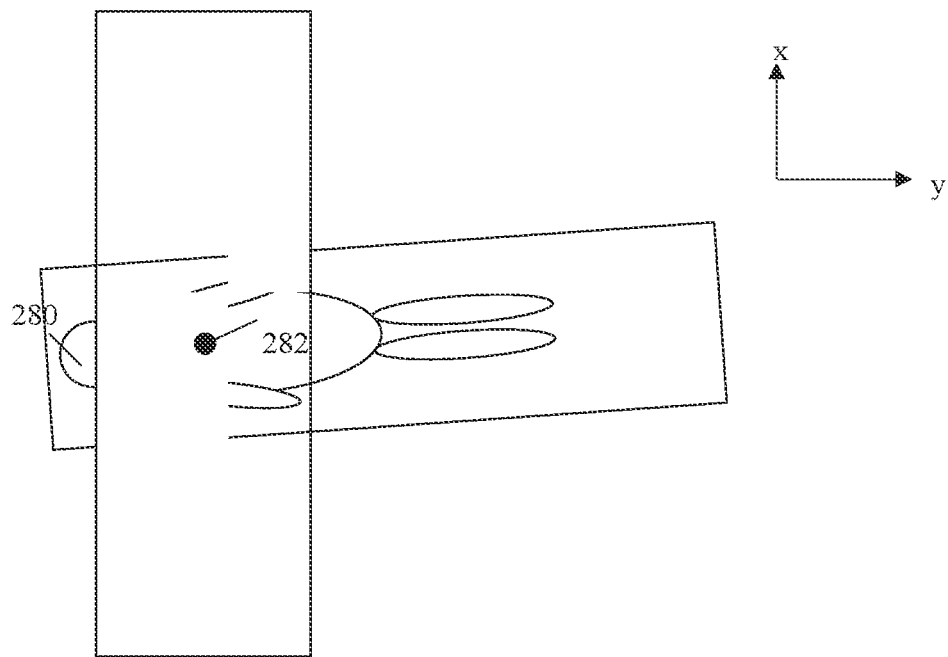

FIG. 13 and FIG. 14 are section views illustrating an exemplary medical device according to some embodiments of the present disclosure. Components of the medical device 1300 may be similar to the medical device 800 in FIG. 8, the descriptions of which may be not repeated.

As shown in FIG. 13 and FIG. 14, a patient support 1410 may be rotatable by an angle along a direction indicated by an arrow b in FIG. 13, thereby achieving a non-coplanar treatment of the object 280 during a radiation treatment of the region 282.

In some embodiments, after the stationary portion 210, the first rotation portion 220, and the second rotation portion 230 are tilted and/or the patient support 1410 is moved, the region 282 of the object 280 to be treated may deviate from the isocenter of the treatment head 570, which may affect the treatment efficacy and/or cause normal tissue of the object 280 to receive unnecessary radiation. In order to solve the problems, the object 280 may be further moved by moving the patient support 1410 such that the center of the region 282 may (substantially) coincide with the isocenter of the treatment head 570. That is, a deviation between the center of the region 282 and the isocenter of the treatment head 570 may be smaller than or equal to a threshold (e.g., a clinically allowable threshold (e.g., 5 millimeters)). It should be noted that the above descriptions are for illustration purposes and non-limiting. As described above, the first rotation portion may be outside the second rotation portion. In some embodiments, the first rotation portion may be inside the second rotation portion, e.g., along a radial direction of the first rotation portion or the second rotation portion.

Figure 15:
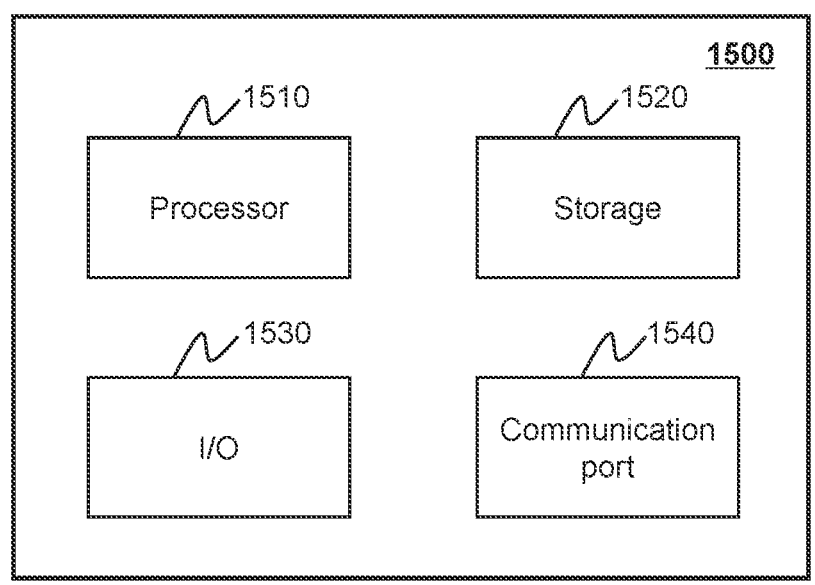
FIG. 15 is a schematic diagram illustrating exemplary hardware and/or software components of a computing device according to some embodiments of the present disclosure.

FIG. 15 is a schematic diagram illustrating exemplary hardware and/or software components of a computing device on which the processing device 120 may be implemented according to some embodiments of the present disclosure. As illustrated in FIG. 15, the computing device 1500 may include a processor 1510, a storage 1520, an input/output (I/O) 1530, and a communication port 1540.

The processor 1510 may execute computer instructions (program code) and perform functions of the processing device 120 in accordance with techniques described herein. The computer instructions may include routines, programs, objects, components, signals, data structures, procedures, modules, and functions, which perform particular functions described herein. For example, the processor 1510 may process data obtained from the medical device 110, the storage device 130, the terminal 140, or any other component of the radiation system 100. In some embodiments, the processor 1510 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 1500. However, it should be noted that the computing device 1500 in the present disclosure may also include multiple processors, thus operations and/or method steps that are performed by one processor as described in the present disclosure may also be jointly or separately performed by the multiple processors. For example, if in the present disclosure the processor of the computing device 1500 executes both step A and step B, it should be understood that step A and step B may also be performed by two different processors jointly or separately in the computing device 1500 (e.g., a first processor executes step A and a second processor executes step B, or the first and second processors jointly execute steps A and B).

The storage 1520 may store data/information obtained from the medical device 110, the storage device 130, the terminal 140, or any other component of the radiation system 100. In some embodiments, the storage 1520 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 1520 may store one or more programs and/or instructions to perform exemplary methods described in the present disclosure.

The I/O 1530 may input or output signals, data, or information. In some embodiments, the I/O 1530 may enable a user interaction with the processing device 120. For example, the processing device 120 may display an image through the I/O 1530. In some embodiments, the I/O 1530 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 1540 may be connected to a network (e.g., the network 150) to facilitate data communications. The communication port 1540 may establish connections between the processing device 120 and the medical device 110, the storage device 130, or the terminal 140. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 1540 may be a standardized communication port, such as RS232, RS485, etc. In some embodiments, the communication port 1540 may be a specially designed communication port. For example, the communication port 1540 may be designed in accordance with the digital imaging and communications in medicine (DICOM) protocol.

Figure 16:
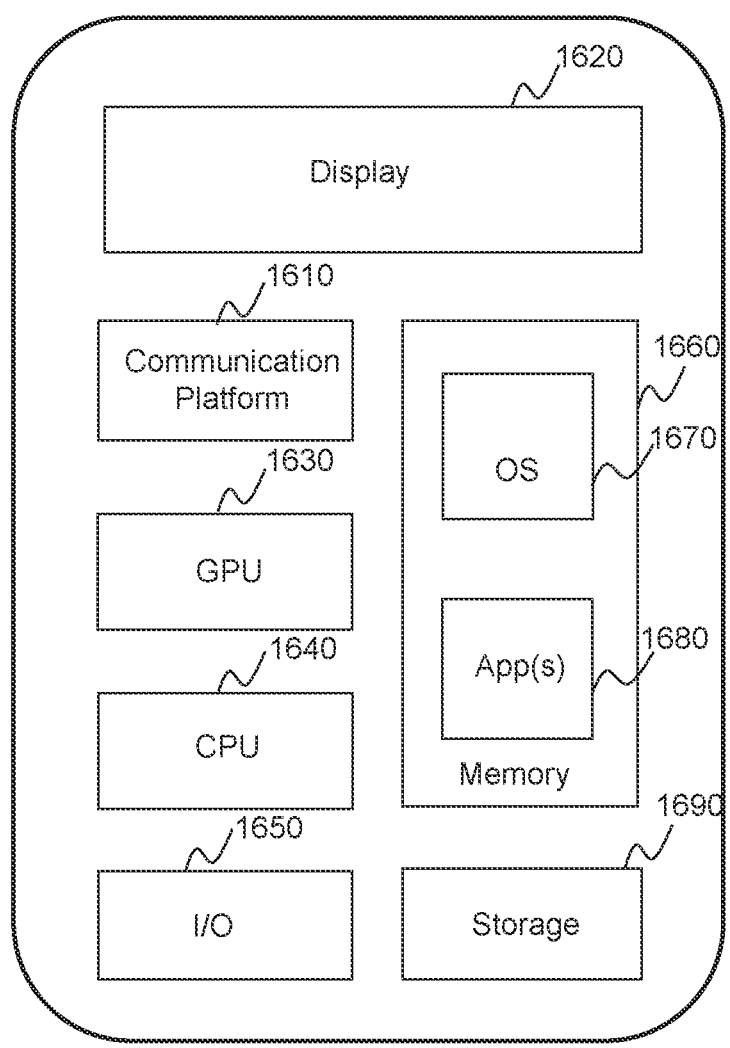
FIG. 16 is a schematic diagram illustrating exemplary hardware and/or software components of a mobile device according to some embodiments of the present disclosure.

FIG. 16 is a schematic diagram illustrating exemplary hardware and/or software components of a mobile device on which the terminal 140 may be implemented according to some embodiments of the present disclosure. As illustrated in FIG. 16, the mobile device 1600 may include a communication platform 1610, a display 1620, a graphics processing unit (GPU) 1630, a central processing unit (CPU) 1640, an I/O 1650, a memory 1660, and a storage 1690. In some embodiments, any other suitable component, including a system bus or a controller (not shown), may also be included in the mobile device 1600. In some embodiments, a mobile operating system 1670 (e.g., iOS, Android, Windows Phone, etc.) and one or more applications 1680 may be loaded into the memory 1660 from the storage 1690 in order to be executed by the CPU 1640. The applications 1680 may include a browser or any other suitable mobile apps for receiving and rendering information relating to radiation therapy or other information from the processing device 120. User interactions with the information stream may be achieved via the I/O 1650 and provided to the processing device 120 and/or other components of the radiation system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the radiation therapy as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 17:
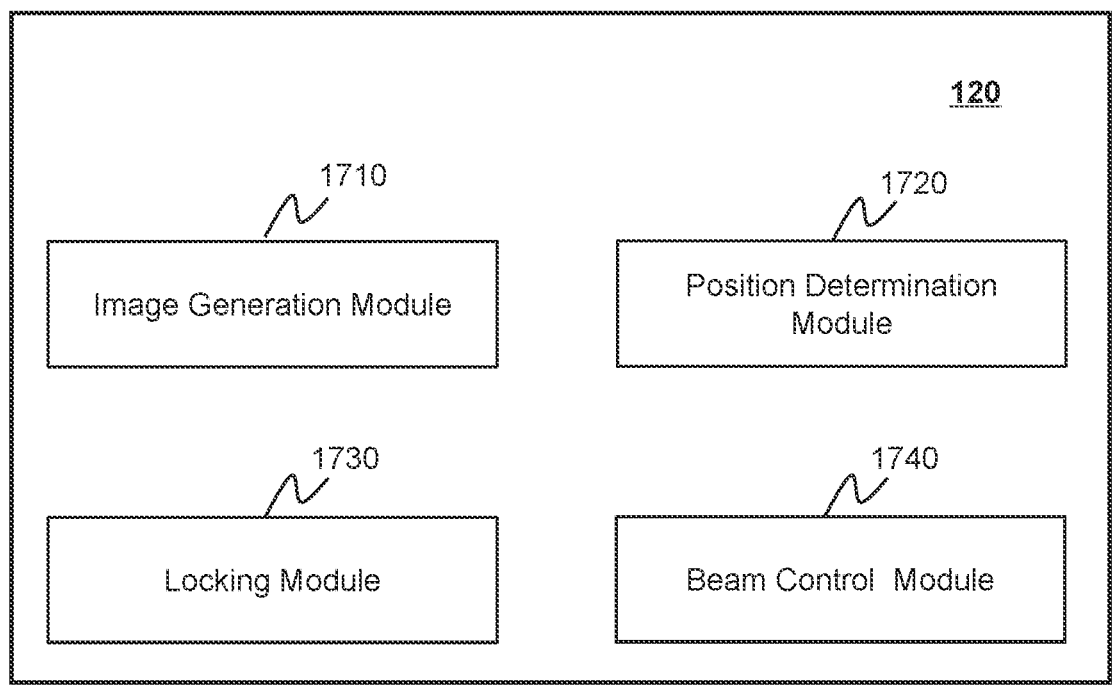
FIG. 17 is a block diagram illustrating an exemplary processing device according to some embodiments of the present disclosure.

FIG. 17 is a block diagram illustrating an exemplary processing device according to some embodiments of the present disclosure. The processing device 120 may include an image generation module 1710, a position determination module 1720, a locking module 1730, and a beam control module 1740.

In some embodiments, a radiation system may include a treatment head, one or more imaging sources, and at least one detector. The treatment head may be configured to deliver a treatment beam towards an object. At least a portion of the treatment head (e.g., a first head portion, the whole treatment head) may be disposed in a first rotation portion or a second rotation portion of the radiation system. The one or more imaging sources may be configured to deliver one or more imaging beams towards the object. At least one of the one or more imaging sources may be disposed in the second rotation portion or the first rotation portion. The at least one detector may be configured to detect at least a portion of the one or more imaging beams. In some embodiments, at least one of the at least one detector may be disposed in the second rotation portion or the first rotation portion. A stationary portion of the radiation system may be connected to the first rotation portion and/or the second rotation portion. The stationary portion may be configured to facilitate a delivery of the treatment beam and/or facilitate a delivery of the one or more imaging beams. The second rotation portion may be configured to rotate independently from the first rotation portion. The radiation system may be similar to the radiation system 100 described in FIGS. 1-14, the descriptions of which are not repeated here.

The imaging generation module 1710 may be configured to generate an image by causing at least one of one or more imaging sources to emit at least one imaging beam toward an object. In some embodiments, the imaging generation module 1710 may use a reconstruction algorithm to generate the image.

In some embodiments, the one or more imaging sources may include a CT imaging source. The imaging generation module 1710 may cause the CT imaging source to emit a CT imaging beam toward the object. The imaging generation module 1710 may obtain an imaging dataset (e.g., projection data) corresponding to at least a portion of the CT imaging beam detected by a detector (e.g., the first detector in FIG. 1) (e.g., a curvilinear detector, a flat panel detector) of the radiation system. The processing device 120 may generate the image based on at least a portion of the imaging dataset.

The position determination module 1720 may be configured to cause a region (e.g., a region to be treated) of the object to be positioned in a radiation system based on the image. In some embodiments, the position determination module 1720 may determine position information (e.g., a position thereof, a contour thereof) of the region of the object based on the image. Further, the position determination module 1720 may cause the region of the object to be positioned in the radiation system according to the position information. In some embodiments, a center of the region may be aligned with an isocenter of the radiation system. For example, the isocenter of the radiation system may include an isocenter of a treatment assembly of the radiation system or an isocenter of an imaging assembly of the radiation system. More descriptions of the positioning of the region of the object may be found elsewhere in the present disclosure, for example, FIG. 18 or the descriptions thereof.

The locking module 1730 may be configured to cause the first rotation portion and the second rotation portion to be locked. In some embodiments, the locking module 1730 may cause a locking component (e.g., the locking component in FIG. 1) or at least one control component (e.g., the at least one control component in FIG. 1) of the radiation system to lock the first rotation portion and the second rotation portion.

In some embodiments, the first imaging source may rotate at a first speed when the second rotation portion rotates independently from the first rotation portion. The first imaging source may rotate at a second speed when the second rotation portion and the first rotation portion rotate synchronously. In some embodiments, the first speed may be larger than the second speed. More descriptions of the locking of the first rotation portion and the second rotation portion may be found elsewhere in the present disclosure, for example, FIG. 18 or the descriptions thereof.

The beam control module 1740 may be configured to cause the treatment head to emit a treatment beam to the region of the object. The treatment beam may be delivered to the region of the object. In some embodiments, the position of the region may change with time due to various motions of organs of the object, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, filling/emptying of bladder, rectum and digestive system, or the like, or any combination thereof. In some embodiments, the whole object may be moved along a direction (e.g., a rotation axis of a radiation device of the treatment system).

In some embodiments, the beam control module 1740 may cause an imaging of the object to be performed during the radiotherapy. The beam control module 1740 may determine whether any change or adjustment is needed with respect to the radiotherapy based on the imaging of the object performed before and/or during the radiotherapy, the descriptions of which may be the same as or similar to FIG. 18 or the descriptions thereof.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided to two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further include a storage module. The storage module may be configured to store data generated during any process performed by any component of the processing device 120. As another example, each of the components of the processing device 120 may include a storage apparatus. Additionally or alternatively, the components of the processing device 120 may share a common storage apparatus.

Figure 18:
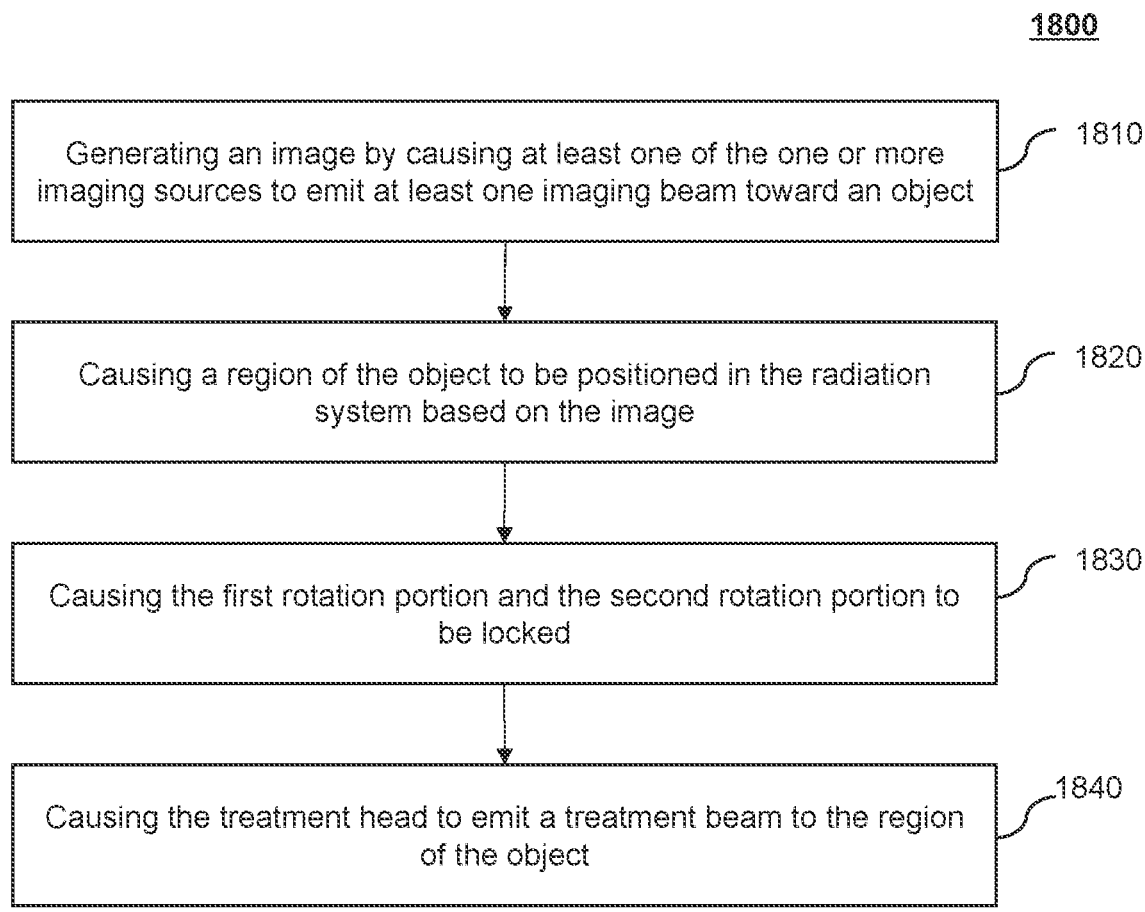
FIG. 18 is a flowchart illustrating an exemplary imaging process of a radiation system according to some embodiments of the present disclosure.

FIG. 18 is a flowchart illustrating an exemplary imaging process of a radiation system according to some embodiments of the present disclosure. The process 1800 may be implemented in the radiation system 100 illustrated in FIG. 1. For example, the process 1800 may be stored in the storage device 130 and/or the storage 1520 in the form of instructions (e.g., an application), and invoked and/or executed by the processing device 120 (e.g., the processor 1510 illustrated in FIG. 15, or one or more modules in the processing device 120 illustrated in FIG. 17). The operations of the illustrated process presented below are intended to be illustrative. In some embodiments, the process 1800 may be accomplished with one or more additional operations not described, and/or without one or more of the operations discussed. Additionally, the order in which the operations of the process 1800 as illustrated in FIG. 18 and described below is not intended to be limiting.

In some embodiments, the radiation system may include a treatment head, one or more imaging sources, and at least one detector. The treatment head may be configured to deliver a treatment beam towards an object. At least a portion of the treatment head (e.g., a first head portion, the whole treatment head) may be disposed in a first rotation portion or a second rotation portion of the radiation system.

The one or more imaging sources may be configured to deliver one or more imaging beams towards the object. At least one of the one or more imaging sources may be disposed in the second rotation portion or the first rotation portion. The at least one detector may be configured to detect at least a portion of the one or more imaging beams. In some embodiments, at least one of the at least one detector may be disposed in the second rotation portion or the first rotation portion. A stationary portion of the radiation system may be connected to the first rotation portion and/or the second rotation portion. The stationary portion may be configured to facilitate a delivery of the treatment beam and/or facilitate a delivery of the one or more imaging beams. The second rotation portion may be configured to rotate independently from the first rotation portion. The radiation system may be similar to the radiation system 100 described in FIGS. 1-14, the descriptions of which are not repeated here.

In 1810, the processing device 120 (e.g., the image generation module 1710) may generate an image (e.g., a 3D image) by causing at least one of the one or more imaging sources to emit at least one imaging beam toward an object. In some embodiments, the processing device 120 may use a reconstruction algorithm to generate the image. For example, the reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

In some embodiments, the one or more imaging sources may include a CT imaging source. The processing device 120 may cause the CT imaging source to emit a CT imaging beam toward the object. The processing device 120 may obtain an imaging dataset (e.g., projection data) corresponding to at least a portion of the CT imaging beam detected by a detector (e.g., the first detector in FIG. 1) (e.g., a curvilinear detector) of the radiation system. The processing device 120 may generate the image based on at least a portion of the imaging dataset.

In 1820, the processing device 120 (e.g., the position determination module 1720) may cause a region (e.g., a region to be treated) of the object to be positioned in the radiation system based on the image. In some embodiments, the processing device 120 may determine position information (e.g., a position thereof, a contour thereof) of the region of the object based on the image. Further, the processing device 120 may cause the region of the object to be positioned in the radiation system according to the position information. In some embodiments, a center of the region may be aligned with an isocenter of the radiation system. For example, the isocenter of the radiation system may include an isocenter of a treatment assembly of the radiation system or an isocenter of an imaging assembly of the radiation system.

In some embodiments, the image may be used to determine a treatment plan of a radiotherapy on the region of the object. In some embodiments, a treatment plan of the object may be determined based on a plan image generated before the image. Since information of the object, for example, a body type of the object, a weight of the object, a size of the object, a position of the region, etc., may change with time, the image may be used to adjust the treatment plan of the region determined based on the plan image. For illustration purposes, the processing device 120 may generate a registration result by registering the image and the plan image and adjust the treatment plan based on the registration result. Merely by way of example, a difference between one parameter (e.g., a position of a tumor, a contour of a tumor) of the treatment plan and a corresponding parameter determined based on the registration result exceeds a threshold, the processing device 120 may adjust the parameter accordingly. As another example, the processing device 120 may supplement at least one new parameter (a position of a newly grown tumor, a contour of a newly grown tumor) determined based on the registration result. In some embodiments, the processing device 120 may identify a change of a position of the region based on a position of the region as represented in the image, compared to a planned position of the region in the plan image. In response to determining that the change exceeds a first threshold, the processing device 120 may cause the region of the object to be placed based on the image or the change. In some embodiments, in response to determining that the change exceeds a second threshold larger than the first threshold, the processing device 120 may determine a new treatment plan based on the image.

In 1830, the processing device 120 (e.g., the locking module 1730) may cause the first rotation portion and the second rotation portion to be locked. In some embodiments, the processing device 120 may cause a locking component (e.g., the locking component in FIG. 1) or at least one control component (e.g., the at least one control component in FIG. 1) of the radiation system to lock the first rotation portion and the second rotation portion. For example, an operator (e.g., an imaging technician) of the radiation system 100 may generate a control signal to make the locking component or the at least one control component to lock the first rotation portion and the second rotation portion. As another example, an operator (e.g., an imaging technician) may operate the locking component or the at least one control component to lock the first rotation portion and the second rotation portion, and the radiation system 100 may detect that the first rotation portion and the second rotation portion are locked.

In some embodiments, the first imaging source may rotate at a first speed when the second rotation portion rotates independently from the first rotation portion. The first imaging source may rotate at a second speed when the second rotation portion and the first rotation portion rotate synchronously. In some embodiments, the first speed is larger than the second speed.

In 1840, the processing device 120 (e.g., the beam control module 1740) may cause the treatment head to emit a treatment beam to the region of the object. The treatment beam may be delivered to the region of the object. In some embodiments, the position of the region may change with time due to various motions of organs of the object, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, filling/emptying of bladder, rectum and digestive system, or the like, or any combination thereof. In some embodiments, the whole object may be moved along a direction (e.g., a rotation axis of a radiation device of the treatment system).

In some embodiments, the processing device 120 may cause an imaging of the object to be performed during the radiotherapy. In some embodiments, the processing device 120 may generate at least one second image by causing at least one of the one or more imaging sources to emit another at least one second imaging beam towards the object. For example, the processing device 120 may generate at least one second imaging dataset by causing the another at least one imaging beam to be delivered to the object by the at least one imaging source at a first time point during the radiotherapy. The processing device 120 may generate the at least one second image based on at least a portion of the at least one second imaging dataset. For example, the processing device 120 may generate a second image (e.g., a 2D image, a 3D image) based on at least a portion of each of the at least one second imaging dataset. As another example, the processing device 120 may generate a second image based on two or more of the at least one third imaging dataset that are from two or more views of the object.

In some embodiments, the processing device 120 may generate the at least one second image by performing a tomosynthesis (also referred to as digital tomosynthesis (DTS)) imaging of the object. Each of the at least one of the one or more imaging sources may only need to rotate within a relatively small angle range to perform the tomosynthesis imaging; that is, the imaging source only needs to rotate for a relatively short time period.

In some embodiments, the one or more imaging sources may include DR imaging sources configured to emit imaging beams that are perpendicular to each other. The processing device 120 may generate the at least one second image by causing the DR imaging sources to emit, towards the object, imaging beams that are perpendicular to each other.

In some embodiments, at least a portion of the treatment beam may be detected by a detector (e.g., the third detector) (e.g., an EPID) to generate a third imaging dataset (e.g., projection data) at a second time point same as or different from the first time point during the radiotherapy. The processing device 120 may generate a third image based on at least a portion of the third imaging dataset.

In some embodiments, the processing device 120 may generate a fourth image based on at least a portion of the third imaging dataset and at least a portion of the at least one second imaging dataset. The image, the at least one second image, the third image, and/or the fourth image may be used to monitor at least one of the position and/or the motion (or movement) of the region during the radiotherapy, a change thereof, or a rate of change thereof.

In some embodiments, the processing device 120 may determine, based on at least one of the image, the at least one second image, the third image, or the fourth image, whether any change or adjustment is needed with respect to the radiotherapy. In some embodiments, when detecting a movement or change of the region, the processing device 120 may adjust a delivery of the treatment beam or a position of the object based on the at least one of the image, the at least one second image, the third image, or the fourth image. For example, the processing device 120 may adjust the delivery of the treatment beam or the position of the object by adjusting at least one machine parameter of a radiation device of the radiation system.

In some embodiments, the processing device 120 may adjust the position of the region with respect to the treatment beam to allow the treatment beam towards the region. In some embodiments, the processing device 120 may adjust a direction of the treatment beam to allow the treatment beam toward the region. In some embodiments, the processing device 120 may adjust the treatment plan (e.g., a radiation dose of the region, a radiation time of the region) and deliver an adjusted treatment beam to the object from the treatment head and based on the adjusted treatment plan. In some embodiments, the processing device 120 may cause the treatment head to pause the delivery of the treatment beam. For example, the processing device 120 may pause the delivery of the treatment beam, and then adjust the treatment head to target at the position of the moved or changed region. As another example, the processing device 120 may pause the delivery of the treatment beam, and then adjust the position of the region with respect to the treatment beam to make the treatment beam target at the region. After the delivery of the treatment beam or the position of the object is adjusted, the treatment head may resume the delivery of the treatment beam.

In some embodiments, when detecting the movement or change of the region, the treatment head may terminate the delivery. In some embodiments, the processing device 120 may generate a notification based on the detected movement or change of the region. In some embodiments, the notification may include information of the movement or change of the region. The notification may be in a form of text, video, audio, etc.

In some embodiments, the processing device 120 may determine whether an unpredicted motion of the object exists based on at least one of the image, the at least one second image, the third image, or the fourth image. In response to determining that an unpredicted motion of the object exists, the processing device 120 may cause the treatment head to pause the delivery of the treatment beam. For instance, the processing device 120 may determine whether the object has ceased a planned breathhold. In response to determining that the object has ceased the planned breathhold, the processing device 120 may cause the treatment head to pause the delivery of the treatment beam.

According to the systems and methods described in the present disclosure, during a radiotherapy on a region, the processing device 120 may automatically generate and/or analyze images (e.g., the image, the at least one second image, the third image, or the fourth image) to record the radiotherapy, monitor the position of the region, assess the change of the position of the region, and/or determine how to proceed further with the radiotherapy (e.g., to continue the radiotherapy as planned, to continue the radiotherapy with a revised plan, or to terminate the radiotherapy, etc.).

In some embodiments, the monitoring, assessment, and/or adjustment may be performed semi-automatically with the input of a user (e.g., a doctor). For example, the processing device 120 may transmit the images to be presented on the terminal 140 (e.g., a display) so that the user may analyze the images and provide an instruction as to how to proceed further with the radiotherapy (e.g., to continue the radiotherapy as planned, to continue the radiotherapy with a revised plan, or to terminate the radiotherapy, etc.). As another example, the processing device 120 may first analyze the images and determine if any change occurs in the region and how much the change is. The processing device 120 may determine accordingly if any adjustment in the radiotherapy is needed. If the change of the region or the adjustment needed in the radiotherapy is within a threshold, the processing device 120 may adjust automatically. In some embodiments, a notification may be generated when the processing device 120 makes such a determination. If the change of the region or the adjustment needed in the radiotherapy is not within a threshold, the processing device 120 may generate a notification to, e.g., the user to seek instructions from the user as to how to proceed further.

In some embodiments, during the radiotherapy, the radiation system may generate a plurality of groups of images (e.g., a plurality of groups of 2D images) of the object, each group at a time point. A group of images may be obtained by causing the one or more imaging sources (e.g., the CT imaging source, the at least one DR imaging source) of the radiation system to emit one or more imaging beams toward the object and the at least one detector to provide views of the object at a time point from different directions/view angles. The radiation system may track, based on the plurality of groups of images, position information (e.g., a position thereof) of the object at different time points. If it is detected that a change of the position information of the target region exceeds a threshold, the radiation system may adjust a delivery of the treatment beam or position information (e.g., a position thereof) of the target region accordingly.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation system comprising:
   a first rotation portion;
   a second rotation portion;
   a treatment head, at least a portion of the treatment head being disposed in the first rotation portion;
   one or more imaging sources, at least one of the one or more imaging sources being disposed in the second rotation portion; and
   at least one detector, wherein
      the second rotation portion is able to rotate independently from the first rotation portion, the first rotation portion is circular, and the first rotation portion is located outside the second rotating portion in a radial direction of the first rotation portion; wherein
         a first component of the first rotation portion and a second component of the second rotation portion are located on a first plane; and
      the treatment head comprises a first portion and a second portion, wherein
         the first component of the first rotation portion includes the first portion of the treatment head, the first portion of the treatment head being configured to emit a treatment beam towards an object; and
         the second component of the second rotation portion includes the second portion of the treatment head, the second portion of the treatment head comprising a collimation component configured to adjust a radiation range of the treatment beam.

2. The radiation system of claim 1, wherein the one or more imaging sources include at least one of:
   a first imaging source configured to emit a first imaging beam towards the object, the first imaging source being disposed in the second rotation portion; or
   at least one second imaging source configured to emit at least one second imaging beam towards the object; and wherein
   the at least one detector includes at least one of:
   a first detector configured to detect at least a portion of the first imaging beam, the first detector being disposed in the second rotation portion; or
   at least one second detector configured to detect at least a portion of the at least one second imaging beam.

3. The radiation system of claim 1, wherein at least two of the imaging sources share one of the at least one detector.

4. The radiation system of claim 2, wherein the at least one second imaging source or the at least one second detector is fixed at a fixed position of a room housing at least a portion of the radiation system or disposed in the second rotation portion without blocking the first imaging beam.

5. The radiation system of claim 2, wherein
   the at least one second detector is disposed in the first rotation portion; and
   the second rotation portion includes at least one opening corresponding to the at least one second detector such that at least a portion of the at least one second imaging beam passes through the at least one opening and impinges on the at least one second detector.

6. The radiation system of claim 2, wherein
   the at least one second imaging source is disposed in the first rotation portion; and
   the second rotation portion includes at least one opening corresponding to the at least one second imaging source such that at least a portion of the at least one second imaging beam passes through the at least one opening.

7. The radiation system of claim 2, wherein the at least one second imaging source is disposed in the second rotation portion.

8. The radiation system of claim 2, wherein the first imaging source rotates independently from the collimation component of the treatment head.

9. The radiation system of claim 1, wherein the second component of the second rotation portion includes at least one of:
   a first imaging source of the one or more imaging sources that is configured to emit a first imaging beam towards the object; or
   a first detector of the at least one detector that is configured to detect at least a portion of the first imaging beam.

10. The radiation system of claim 1, wherein a collimation component of the treatment head is disposed in the first rotation portion.

11. The radiation system of claim 1, wherein
    the second rotation portion includes an opening; and
    one or more components of the first rotation portion is movable into the opening, the one or more components of the first rotation portion including at least one of a treatment source, a jaw, a chamber, a primary collimator, or a secondary collimator of the treatment head.

12. The radiation system of claim 1, wherein the collimation component and a first imaging source are arranged along a circumference of the second rotation portion.

13. The radiation system of claim 1, wherein
    the collimation component and a first imaging source are arranged parallel along a rotation axis of the second rotation portion;
    the first imaging source is movable to a first position such that the first imaging source of the one or more imaging sources corresponds to a region of an object to be imaged during an imaging of the object; or the collimation component is movable to a second position such that the collimation component corresponds to a region of an object to be treated during a radiation treatment of the object.

14. The radiation system of claim 1, wherein
the collimation component of the treatment head is connected to the first rotation portion; and
the collimation component is movable to a third position of the second rotation portion such that a position of the treatment beam emitted by the treatment head corresponds to the third position of the collimation component.

15. The radiation system of claim 1, wherein the second rotation portion and the first rotation portion are able to rotate synchronously.

16. The radiation system of claim 1, wherein
at least one of a third component of the first rotation portion and a fourth component of the second rotation portion are located on at least one second plane that is different from the first plane, the third component of the first rotation portion being different from the first component, and the fourth component of the second rotation portion being different from the second component.

17. The radiation system of claim 16, wherein the third component or the fourth component includes at least one of:
a microwave device configured to facilitate a delivery of the treatment beam;
an acceleration device configured to accelerate an electron beam to generate the treatment beam;
a cooling device configured to cool at least one component of the treatment head; or
a high-voltage device configured to facilitate a delivery of one or more imaging beams by the one or more imaging sources.

18. The radiation system of claim 1, wherein
the one or more imaging sources include at least two imaging sources; and
the at least two imaging sources are configured to emit at least two imaging beams of different energy levels.

19. A radiation system comprising:
a first rotation portion;
a second rotation portion;
a treatment head comprising a first portion configured to emit a treatment beam towards an object and a second portion configured to adjust a radiation range of the treatment beam, the second portion of the treatment head being movable with respect to the first portion of the treatment head, and the first portion of the treatment head being disposed in the first rotation portion;
one or more imaging sources, at least one of the one or more imaging sources being disposed in the second rotation portion; and
at least one detector, wherein
the second rotation portion is able to rotate independently from the first rotation portion, the first rotation portion is circular, and the first rotation portion is located outside the second rotating portion in a radial direction of the first rotation portion; wherein
a first component of the first rotation portion and a second component of the second rotation portion are located on a first plane; the first component of the first rotation portion includes the first portion of the treatment head; and
the second component of the second rotation portion includes the second portion of the treatment head, the second portion of the treatment head comprising a collimation component configured to adjust the radiation range of the treatment beam.

20. A system, comprising:
at least one storage device including a set of instructions;
at least one processor in communication with the at least one storage device and a radiation system, wherein the radiation system includes:
a first rotation portion;
a second rotation portion;
a treatment head, at least a portion of the treatment head being disposed in the first rotation portion;
one or more imaging sources, at least one of the one or more imaging sources being disposed in the second rotation portion; and
at least one detector, wherein
when executing the set of instructions, the at least one processor is configured to cause the system to perform operations including:
causing the second rotation portion to rotate independently from the first rotation portion, wherein the first rotation portion is circular, and the first rotation portion is located outside the second rotating portion in a radial direction of the first rotation portion;
generating an image by causing the at least one of the one or more imaging sources to emit at least one imaging beam toward an object;
causing a region of the object to be positioned in the radiation system based on the image;
causing the first rotation portion and the second rotation portion to rotate synchronously; and
causing the treatment head to emit a treatment beam to the region of the object; wherein
a first component of the first rotation portion and a second component of the second rotation portion are located on a first plane; and
the treatment head comprises a first portion and a second portion, wherein
the first component of the first rotation portion includes the first portion of the treatment head, the first portion of the treatment head being configured to emit the treatment beam towards the object; and
the second component of the second rotation portion includes the second portion of the treatment head, the second portion of the treatment head comprising a collimation component configured to adjust a radiation range of the treatment beam.

* * * * *